US011608363B2

(12) United States Patent
Chappell et al.

(10) Patent No.: US 11,608,363 B2
(45) Date of Patent: Mar. 21, 2023

(54) MATERIALS AND METHODS FOR CELL-FREE EXPRESSION OF VACCINE EPITOPE CONCATEMERS

(71) Applicant: Leidos, Inc., Reston, VA (US)

(72) Inventors: Stephen A. Chappell, San Diego, CA (US); Vincent P. Mauro, San Diego, CA (US); John Dresios, Carlsbad, CA (US)

(73) Assignee: Leidos, Inc, Reston, VA (US)

( * ) Notice: Subject to any disclaimer, the term of this patent is extended or adjusted under 35 U.S.C. 154(b) by 490 days.

(21) Appl. No.: 16/459,574

(22) Filed: Jul. 1, 2019

(65) Prior Publication Data

US 2020/0010512 A1    Jan. 9, 2020

Related U.S. Application Data

(60) Provisional application No. 62/693,904, filed on Jul. 3, 2018.

(51) Int. Cl.
*A61K 39/00*    (2006.01)
*C07K 14/31*    (2006.01)
*G01N 33/569*    (2006.01)

(52) U.S. Cl.
CPC ....... *C07K 14/31* (2013.01); *G01N 33/56938* (2013.01); *A61K 39/00* (2013.01); *G01N 2333/31* (2013.01)

(58) Field of Classification Search
CPC ........ A61K 38/00; A61K 38/10; A61K 38/16; A61K 39/00
USPC ................................ 424/184.1, 185.1, 192.1
See application file for complete search history.

(56) References Cited

U.S. PATENT DOCUMENTS

| | | | |
|---|---|---|---|
| 6,780,607 B2 | 8/2004 | Choi et al. | 435/68.1 |
| 7,338,789 B2 | 3/2008 | Swartz et al. | 435/71.2 |
| 8,034,581 B2 | 10/2011 | Hara et al. | 435/68.1 |
| 8,357,529 B2 | 1/2013 | Swartz et al. | 435/317.1 |
| 9,908,064 B2 | 3/2018 | Dresios et al. | |
| 2007/0218075 A1 | 9/2007 | Matsuka et al. | |
| 2013/0280797 A1 | 10/2013 | Rao et al. | 435/288.7 |
| 2015/0110836 A1 | 4/2015 | Glanville | |
| 2016/0230203 A1* | 8/2016 | Dresios | B01D 15/14 |
| 2016/0339078 A1 | 11/2016 | Hamill et al. | |
| 2019/0048379 A1* | 2/2019 | Kvam | C12P 19/34 |

OTHER PUBLICATIONS

Zheng et al. Methods Mol. Biol. 434: 205-219, 2008.*
Gurusamy et al. PLoS One 12(8): e0182367, pp. 1/23 to 23/23, Aug. 11, 2017.*
Sullivan et al. In: Methods in Molecular Biology, Clifton, N.J., Chapter 8, pp. 95-107, Jan. 2018.*
Sullivan et al. Biotechnol. J. 11:238-248, 2016.*
Mirzadegan et al. Biochemistry 42: 2759-2767, pp. 1-15, 2003.*
Yanagihara et al. J. Immunoassay & Immunochemistry 29: 181-196, 2008.*
Sullivan et al. Biotechnol. J. 11: 238-248, online pub Oct. 2, 2015.*
Spirin, A. S., "High-throughput Cell-Free Systems For Synthesis of Functionally Active Proteins," *Trends Biotechnol.* 22:538-545, 2004.
Gilbert, M. and Albala, J. S., "Accelerating Code to Function: Sizing Up the Protein Production Line," *Curr. Opin. Chem. Biol.* 6:102-105, 2002.
Mei, Q., Frederickson, C. K., Simon, A., et al., "Cell-Free Protein Synthesis in Microfluidic Array Devices," *Biotechnol. Prog.* 23:1305-1311, 2007.
Goerke, Aaron R. and Swartz, James R., "Development of Cell-Free Protein Synthesis Platforms For Disulfide Bonded Proteins," *Biotechnol. Bioeng.* 99:351-367, 2008.
Yang, Junhao, et al., "Rapid Expression of Vaccine Proteins for B-Cell Lymphoma in a Cell-Free System," *Biotechnol. Bioeng.* 89:503-511, 2005.
Yin, Gang, et al., "Aglycosylated Antibodies and Antibody Fragments Produced in a Scalable in Vitro Transcription-Translation System," *MAbs.* 4:217-225, 2012.
Kline et al., "Methods to Make Homogenous Antibody Drug Conjugates," *Pharm. Res.*, PMID:25511917, 2014.
Carlson, E. D., et al., "Cell-Free Protein Synthesis Applications Come of Age," *Biotechnol. Adv.* 30:1185-1194, 2012.
Katzen, F., et al., "The Past, Present and Future of Cell-Free Protein Synthesis," *Trends Biotechnol.* 23:150-156, 2005.
Swartz, Jim, "Developing Cell-Free Biology for Industrial Applications," *J. Ind. Microbiol. Biotechnol.* 33:476-485, 2006.
Zawada, James F., et al., "Microscale to Manufacturing Scale-Up of Cell-Free Cytokine Production—A New Approach for Shortening Protein Production Development jTimelines," *Biotechnol. Bioeng.* 108:1570-1578, 2011.
Shirokov, V.A., et al., "Continuous-Exchange Protein-Synthesizing Systems," *Methods Mol. Biol.* 375:19-55, 2007.
Kim, Dong-Myung and Swartz, James R., "Regeneration of Adenosine Triphosphate From Glycolytic Intermediates For Cell-Free Protein Synthesis," *Biotechnol. Bioeng.* 74:309-316, 2001.
Jewett, M. C. and Swartz, J. R., "Mimicking the *Escherichia coli* Cytoplasmic Environment Activates Long-Lived and Efficient Cell-Free Protein Synthesis," *Biotechnol. Bioeng.* 86:19-26, 2004.
Jewett, Michael C., et al., "An Integrated Cell-Free Metabolic Platform For Protein Production and Synthetic Biology," *Mol. Syst. Biol.* 4, DOI: 10.1038/msb, 2008.
Zawada, J. F. and Swartz, J. R., "Maintaining Rapid Growth in Moderate-Density *Escherichia coli* Fermentations," *Biotechnol. Bioeng.* 89:407-415, 2005.
Schoborg, Jennifer A., et al., "Substrate Replenishment and Byproduct Removal Improve Yeast Cell-Free Protein Synthesis," *Biotechnol J.* 9:630-640, 2014.

(Continued)

*Primary Examiner* — S. Devi
(74) *Attorney, Agent, or Firm* — Dawn-Marie Bey; Bey & Cotropia PLLC

(57) ABSTRACT

The present disclosure provides materials and methods for cell-free expression of epitopes for immunotherapy applications. In particular, the present disclosure provides materials and methods for expressing concatenated epitopes using a cell-free protein synthesis platform for high throughput, large scale, and unbiased epitope screening and the generation of multi-epitope vaccines.

14 Claims, 8 Drawing Sheets

Specification includes a Sequence Listing.

(56) References Cited

OTHER PUBLICATIONS

Hodgman, C. E. and Jewett, M. C., "Optimized Extract Preparation Methods and Reaction Conditions For Improved Yeast Cell-Free Protein Synthesis," *Biotechnol. Bioeng.* 110:2643-2654, 2013.

Aoki, M., et al., "Automated System For High-Throughput Protein Production Using the Dialysis Cell-Free Method," *Protein Expr. Purif.* 68:128-136, 2009.

Makino, S., et al., "Cell-Free Protein Synthesis Technology in NMR High-Throughput Structure Determination," *Methods Mol. Biol.* 607:127-147, 2010.

Arnau, J., et al., "Current Strategies For the Use of Affinity Tags and Tag removal For the Purification of Recombinant Proteins," *Protein Expr. Purif.* 48:1-13, 2006.

Mei, Qian, et al., "Protein Synthesis in a Device With Nanoporous Membranes and Microchannels," *Lab Chip.* 10:2541-2545, 2010.

Yamamoto, T., et al., "Evaluation of Cell-Free Protein Synthesis Using PDMS-Based Microreactor Arrays," *Anal. Sci.* 24:243-246, 2008.

Murtas, G., et al., "Protein Synthesis in Liposomes With a Minimal Set of Enzymes," *Biochem. Biophys. Res. Commun.* 363:12-17, 2007.

Iskakova, Madina B., et al., "Troubleshooting Coupled in vitro Transcription-Translation System Derived From *Escherichia coli* Cells: Synthesis of High-Yield Fully Active Proteins," *Nucleic Acids Res.* vol., 34, No. 19, e135, 2006.

Brandi, Letizia, et al., "Assays For the Identification of Inhibitors Targeting Specific Translational Steps," *Methods Mol Med.* 142:87-105, 2008.

Chirino, A. J. and Mire-Sluis, A., "Characterizing Biological Products and Assessing Comparability Following Manufacturing Changes," *Nat. Biotechnol.* 22:1383-1391, 2004.

Leader, B., et al., "Protein Therapeutics: A Summary and Pharmacological Classification," *Nat. Rev. Drug. Discov.* 7:21-39, 2008.

Mocini, D., et al., "Structure, Production and Function of Erythropoietin: Implications For Therapeutical Use in Cadiovascular Disease," *Curr. Med. Chem.* 14:2278-2287, 2007.

Metcalf, D., "The Molecular Biology and Functions of the Granulocyte Macrophage Colony Stimulating Factors," *Blood.* 67:257-67, 1986.

Gan, R. and Jewett, Michael C., "A Combined Cell-Free Trancsription-Translation System From *Saccharomyces cerevisiae* for Rapid and Robust Protein Synthesis," *Biotechnol. J.* 9:641-651, 2014.

Bundy, B. C. and Swartz, J. R., "Site-Specific Incorporation of p-propargyloxyphenylalanine in a Cell-Free Environment For Direct Protein-Protein Click Conjugation," *Bioconjug. Chem.* 21:255-263, 2010.

Kitamura, T., et al., "Identification and Analysis of Human Erythropoietin Receptors on a Factor-Dependent Cell Line, TF-1," *Blood* 73:375-380, 1989.

Young, Carissa L., et al., "Recombinant Protein Express and Purification: A Comprehensive Review of Affinity Tags and Microbial Applications," *Biotechnol. J.* 7:620-634, 2012.

Mortimer, R. K. and Johnston, J. R., "Genealogy of Principal Strains of the Yeast Genetic Stock Center," *Genetics,* 113:35-43, 1986.

Walter, P., et al., "The Protein Translocation Machinery of the Endoplasmic Reticulum," *Philos. Trans. R. Soc. Lond. B. Biol. Sci.* 300:225-228, 1982.

Walter, P., et al., "Protein Translocation Across the Endoplasmic Reticulum," *Cell,* 38:5-8, 1984.

Walter, P. and Blobel, G., "Preparation of Microsomal Membranes for Cotranslational Protein Translocation," *Methods Enzymol.* 96:84-93, 1983.

Lajoie, M. J., et al., "Genomically Recoded Organisms Expand Biological Functions," *Science,* 342:357-360, 2013.

Kim, T. W., et al., "Simple Procedures For the Construction of a Robust and Cost-Effective Cell-Free Protein Synthesis System," *J. Biotechnol.* 126:554-561, 2006.

Matsuda, Daiki and Mauro, Vincent P., "Determinants of Initiation Codon Selection During Translation in Mammalian Cells," *PLoS One,* 5:1-13, DOI: 10.1371/journal.pone.0015057, 2010.

Chappell, S. A., et al., "Ribosomal Tethering and Clustering as Mechanisms For Translation Initiation," *Proc. Natl. Acad. Sci. U.S.A.* 103:18077-18082, 2006.

Dayhoff, M. O., "Atlas of Protein Sequence and Structure," vol. 5, National Biomedical Research Foundation, pp. 101-110, 1972.

Dayhoff, M. O., "Atlas of Protein Sequence and Structure," vol. 5, Supplement 2, National Biomedical Research Foundation, pp. 1-10, 1976.

Kigawa, "Cell-Free Protein Preparation Through Prokaryotic Transcription-Translation Methods,"In Cell-Free Protein Production: Methods and Protocols, Endo, et al., Methods in Molecular Biology, vol. 607, Humana Press, New York, NY, pp. 1-10, 2010.

Mehlin, C., et al., "Heterologous expression of proteins from Plasmodium falciparum: results from 1000 genes," Mol. Biochem. Parasitol., 148(2), pp. 144-160, 2006.

Oprea, M. and Antohe, F., "Reverse-vaccinology strategy for designing T-cell epitope candidates for *Staphylococcus aureus* endocarditis vaccine," Biologicals, 41, pp. 148-153, 2013.

Kwon, Y-C, Jewett, M. C., "High-throughput preparation methods of crude extract for robust cell-free protein synthesis," Sci. Rep. 5: 8663, DOI: 10.1038/srep08663, 2015.

"Epitope Mapping Protocols in Methods in Molecular Biology," vol. 66, G. E. Morris, Ed., 1996.

International Search Report and Written Opinion for PCT Application No. PCT/US19/40210, dated Nov. 25, 2019, 20 pp.

F. Xian, et al., "Peptide Biosynthesis With Stable Isotope Labeling From a Cell-Free Expression System for Targeted Proteomics With Absolute Quantification," Molecular & Cellular Proteomics, vol. 15(8), pp. 2819-2828, 2016.

J. Ahn, et al., "Use of Signal Sequences as an In Situ Removable Sequence Element to Stimulate Protein Synthesis in Cell-Free Extracts," Nucleic Acids Research, vol. 35, No. 4, doi: 10.1093/nar/gk1917, 8 pp., 2007.

"Hypothetical Protein fnb [imported]—*Staphylococcus aureus* (strain N315)," [online], [retrieved Sep. 3, 2019], PIR: H90053, 1 p., Retrieved From the Internet: https://www.ncbi.nlm.nih.gov/protein/25507937?report=genpept.

H. Takeda, et al., "CP5 system, for simple and highly efficient protein purification with a C-terminal designed mini tag," PLOS One 12(5): e0178246, https://doi.org/10.1371/journal.pone.0178246, 18 pp., May 25, 2017.

R. Narumi, et al., "Cell-free synthesis of stable isotope-labeled internal standards for targeted quantitative proteomics," Synthetic and Systems Biotechnology, vol. 3(2), pp. 97-104, 2018.

S. Buus, et al., "High-resolution Mapping of Linear Antibody Epitopes Using Ultrahigh-density Peptide Microarrays," Molecular & Cellular Proteomics, vol. 11(12), pp. 1790-1800, 2012.

European Search Report for EP App. No. 19830364.6, dated Mar. 25, 2022, 7 pp.

Stefan Haberstock, et al., "A Systematic Approach to Increase the Efficiency of Membrane Protein Production in Cell-Free Expression Systems," Protein Expression and Purification, vol. 82, No. 2, pp. 308-316, XP028477053, ISSN: 1046-5928, DOI: 10.1016/J.PEP. 2012.01.2018 [retrieved on Feb. 8, 2012].

* cited by examiner

MATERIALS AND METHODS FOR CELL-FREE EXPRESSION OF VACCINE EPITOPE CONCATEMERS

RELATED APPLICATIONS

This application claims priority to and the benefit of U.S. Provisional Patent Application No. 62/693,904, filed Jul. 3, 2018. This application is incorporated herein by reference in its entirety and for all purposes.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 21,328 Byte ASCII (Text) file named "LEID0010-PRO4_ST25," created on Jun. 27, 2019.

FIELD

Provided herein are materials and methods for cell-free expression of epitopes for vaccine applications. In particular, the present disclosure provides materials and methods for expressing concatenated epitopes using a cell-free protein synthesis platform for high throughput, large scale, and unbiased epitope screening and the generation of multi-epitope vaccines.

BACKGROUND

At present, production of protein biologics is primarily realized in cell-based prokaryotic and eukaryotic expression systems, including bacterial, yeast, and mammalian cells. However, these systems require multiple processes, large bioreactors, lengthy production cycles, laborious purification protocols, specialized facilities, and high costs. In addition, cell-based production approaches suffer from factors that affect cell viability, therefore they are not suitable for expressing toxic proteins or peptides that can be deleterious to the host when expressed at high levels. Furthermore, these approaches are impractical for employment at the point of need due to their stringent requirements for optimum cell growth, dedicated facilities and long end-to-end processes. Recent advances in synthetic biology have allowed the development of prokaryotic and eukaryotic cell-free protein synthesis (CFPS) systems amenable to rapid, flexible, adaptable, and cost-effective manufacture of protein and peptide products. These systems do not depend on cell viability and allow the direction of energy resources toward the expression of specific protein targets as well as high yield expression of proteins that could otherwise be toxic to the host.

Such CFPS systems can be useful in many protein and peptide expression contexts including, for example, epitope screening applications. Currently, expression of antigenic peptides for vaccine screening is challenging due to the poor and/or variable expression of predicted epitopes. In this respect, the value of a screen is severely minimized if only a small fraction of the proteins can be expressed at detectable levels, or if the detectable proteins are expressed at dramatically different levels. Robust, balanced expression of candidate epitopes will likely lead to efficient discovery of vaccine candidates. To this end, there is a need for CFPS systems and platforms that facilitate efficient and robust protein and peptide expression and enable rapid, high-throughput vaccine epitope screening.

SUMMARY

Embodiments of the present disclosure include materials and methods for expressing concatenated epitopes using a cell-free protein synthesis platform for high throughput, large scale, and unbiased epitope screening and the generation of multi-epitope vaccines.

Embodiments of the present disclosure include a protein expression cassette that includes two or more concatenated epitopes, a heterologous promoter upstream of the two or more concatenated epitopes, an N-terminal peptide tag, and a C-terminal peptide tag. In some embodiments, the two or more concatenated epitopes comprise the polypeptide of SEQ ID NO: 1. In some embodiments, the two or more concatenated epitopes comprise the polypeptide of SEQ ID NO: 9. In other embodiments, the two or more concatenated epitopes comprise the polypeptide of SEQ ID NO: 17. In other embodiments, the two or more concatenated epitopes comprise the polypeptide of SEQ ID NO: 25. In other embodiments, the two or more concatenated epitopes comprise the polypeptide of SEQ ID NO: 34. In some embodiments, the two or more concatenated epitopes comprise the polypeptide of SEQ ID NO: 34. In some embodiments, the two or more concatenated epitopes comprise any combination of SEQ ID NOs: 2-8, 10-16, 18-24, 26-33, and 35-41.

In some embodiments, the two or more concatenated epitopes comprise a polypeptide having a sequence that is about 70% identical to SEQ ID NOs: 1, 9, 17, 25, or 34. In some embodiments, the two or more concatenated epitopes comprise a polypeptide having a sequence that is about 80% identical to SEQ ID NOs: 1, 9, 17, 25, or 34. In some embodiments, the two or more concatenated epitopes comprise a polypeptide having a sequence that is about 85% identical to SEQ ID NOs: 1, 9, 17, 25, or 34. In some embodiments, the two or more concatenated epitopes comprise a polypeptide having a sequence that is about 90% identical to SEQ ID NOs: 1, 9, 17, 25, or 34. And in some embodiments, the two or more concatenated epitopes comprise a polypeptide having a sequence that is about 95% identical to SEQ ID NOs: 1, 9, 17, 25, or 34.

Embodiments of the present disclosure also include a method of producing a plurality of epitopes. In accordance with these embodiments, the method includes expressing a plurality of epitopes using a cell-free protein synthesis (CFPS) platform and any of the protein expression cassettes provided herein, and isolating or purifying the plurality of epitopes.

Embodiments of the present disclosure also include a method of identifying an immunogenic epitope. In accordance with these embodiments, the method includes producing a plurality of candidate epitopes using a cell-free protein synthesis (CFPS) platform of the present disclosure, and exposing the plurality of candidate epitopes to a sample comprising at least one antibody.

In some embodiments, the method further includes assessing immunogenicity of the plurality of candidate epitopes by measuring reactivity of the plurality of candidate epitopes with the at least one antibody. In some embodiments, the plurality of candidate epitopes originates from a single organism or from multiple organisms. In some embodiments, the plurality of candidate epitopes originates from the same protein or from different proteins. Embodiments of the present disclosure also include a multi-epitope vaccine comprising the plurality of candidate epitopes demonstrating immunogenicity.

DETAILED DESCRIPTION

Figure 1:
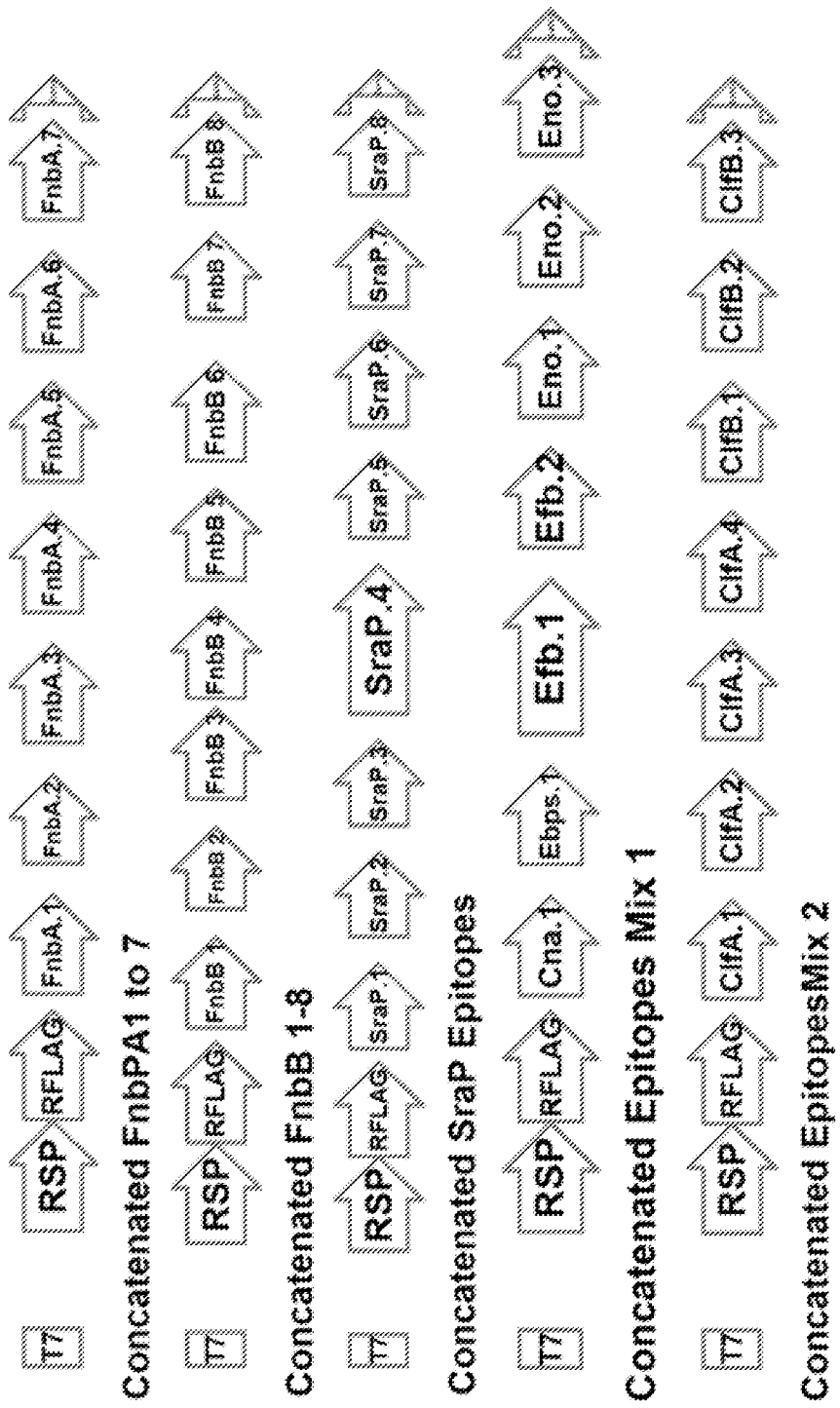
FIG. 1 includes a representative schematic of concatenated epitopes, according to one embodiment of the present disclosure. Exemplary embodiments include the expression of concatenated epitopes as a single peptide containing a signal peptide (RSP) and a 3× FLAG tag (RFLAG) fusion at the N-terminus, and a His-tag (6×His) fused at the C-terminus, under the control of a T7 promoter. Each epitope is separated by a six-amino acid spacer, with each spacer generated by the inclusion of three amino acids that flank each epitope in their original context.

Provided herein are materials and methods for cell-free expression of epitopes for vaccine screening and novel vaccine synthesis applications. In particular, the present disclosure provides materials and methods for expressing concatenated epitopes using a cell-free protein synthesis platform for high throughput, large scale, and unbiased epitope screening and the generation of multi-epitope vaccines.

Embodiments of the present disclosure include the use of a cell-free protein synthesis (CFPS) platform for rapid protein production from DNA templates that do not require cell cultures or insertion of DNA sequences into cells. In accordance with these embodiments, the expression system can be manipulated and optimized, thus avoiding the unpredictability of living systems. The cell-free reaction utilizes low cost lysates from engineered eukaryotic cells (e.g., yeast or mammalian) and prokaryotic (e.g., bacterial) strains that contain factors for protein folding and posttranslational modifications. The freedom of design afforded by cell-free production enables eukaryotic and prokaryotic lysates to be used interchangeably for expression of difficult protein targets. This flexibility yields a general expression platform that scales from two to hundreds of protein biologics, because different proteins can be expressed preferentially in either eukaryotic or prokaryotic systems by simply changing template DNA input. The platform concept also combines an in-line flexible configuration of posttranslational, purification (e.g., ion exchange, size exclusion and affinity chromatography), formulation and characterization modules for efficient production of active protein or peptide product depending on target requirements. This integrated process allows flexibility for purification of different target proteins on same platform. Such modularity also offers scalability through parallelization.

In some embodiments, the cell free expression system can be used for vaccine epitope screens as well as for the generation of multi-epitope vaccines. For this application, both expression levels and uniformity of expression of different peptide sequences is important. This approach uses the expression of concatenated epitopes identified using reverse vaccinology approaches for rapid epitope screening as well as synthesis of novel vaccines containing multiple epitopes from different proteins, multiple epitopes from the same protein, multiple epitopes from the same organism, or custom vaccines containing multiple epitopes from different organisms.

In accordance with these embodiments, *Staphylococcus aureus* (*S. aureus*) was identified as a suitable pathogen for a cell-free based epitope screen as well as multi-epitope vaccine development. Approximately 20% of people are persistently colonized with *S. aureus* bacterium but have no symptoms. When symptoms of *S. aureus* infection do manifest, they can lead to various inflammatory diseases that range in seriousness from skin infections to severe infections such as infective endocarditis, which can be fatal. Due to the severity of *S. aureus* endocarditis, antibiotic prophylaxis is considered to be an important therapeutic option, especially for patients in high risk groups. However, *S. aureus* rapidly evolves resistance, and there are methicillin-resistant (MRSA) strains spreading in hospitals and the community. A search for alternative treatment approaches includes vaccines, therapeutic antibodies, and novel anti-microbial therapies. *S. aureus* produces several virulence factors and efforts to develop effective vaccines have been largely unsuccessful. Current reports indicate that all *S. aureus* vaccine trials have failed. The consensus is that a multivalent vaccine that reflects the genetic diversity of *S. aureus* species will be superior to a monovalent vaccine.

Various efforts to develop vaccines have focused mainly on B-cell immunity and the development of opsonic antibodies; however, recent information suggests that cell mediated immunity may be needed for effective protection. Therefore, embodiments of the present disclosure include expression of epitopes that are predicted to activate both B-cell and T-cell (MHC I and MHC II) mediated immunity. A Reverse Vaccinology approach was taken to predict epitopes based on protein features that may indicate antigenicity, including extracellular localization, presence of a signal peptide, and B-cell epitope sequences. Ten candidate proteins were then filtered based on other desirable attributes, including location on the outer membrane and various virulence factors that are involved in bacterial attachment were analyzed including evidence that these proteins have a role in endocarditis (e.g., clumping factors A and B), fibronectin binding proteins A and B, and collagen adhesion. B-cell epitope prediction analyses was performed for these proteins followed by analyses to identify promiscuous T-cell epitopes within these same B-cell epitopes.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Complementary" refers to the characteristic of two or more structural elements (e.g., peptide, polypeptide, nucleic acid, small molecule, etc.) of being able to hybridize, dimerize, or otherwise form a complex with each other. For example, a "complementary peptide and polypeptide" are capable of coming together to form a complex. Complementary elements may require assistance to form a complex (e.g., from interaction elements), for example, to place the elements in the proper conformation for complementarity, to co-localize complementary elements, to lower interaction energy for complementary, etc.

"Concatenate" or "concatenated", as used herein, refers to the joining of fragments to one another in a random order and orientation to produce a concatenation product (e.g., single molecule in which the initial fragments, or copies thereof, are covalently linked to one another, either directly or indirectly). The term "concatenated DNA," or "concatenated cassette" as used herein, refers to a product of concatenating fragments of DNA to one another. Such a molecule may contain at least 2, at least 3, at least 5, at least 10, at least 50, at least 100, at least 500, or at least 1000 fragments that are joined to one another, either directly or indirectly (e.g., via a linker or spacer region). A concatenated molecule may be linear or circular. DNA fragments may be concatenated by ligation or overlap extension, for example.

"Cell-free system" as used herein generally refers to any system capable of translating a polynucleotide into a peptide, polypeptide, and/or protein that does not take place in an intact cell. Cell-free systems that can be used in the present disclosure include, but are not limited to, protein expression components from eukaryotic, prokaryotic, and/or viral sources. For example, cell-free systems as used herein can include mammalian and/or bacterial protein expression systems derived from mammalian and/or bacterial lysates. Sources of lysate having protein expression components include, but are not limited to, fungi, bacteria, mammalian cells (e.g., reticulocytes, endothelial cells, and lymphocytes), immortalized cell lines (e.g., cancer cell lines, CHO cell lines, etc.), and plant cells (such as wheat germ or embryo cells, etc.). In some embodiments, cell-free systems of the present disclosure include cell-free transcription and translation systems that are coupled. For example, coupled transcription/translation systems and coupled cell-free protein synthesis systems can include processes whereby transcription and translation steps are carried out in sequence in a cell-free system, whereas uncoupled cell-free protein synthesis systems and cell-free translation systems are processes whereby the transcribed mRNA is purified after the initial transcription step and then the purified mRNA is transferred to a separate reaction system in which protein synthesis takes place.

"Derivative of" or "derived from" a parent peptide or polypeptide as used herein describes an amino acid sequence that is homologous, but not identical, to the parent peptide or polypeptide. A peptide may be or represent a fragment of the parent protein or polypeptide.

"Epitope" as used herein refers to a peptide or polypeptide that can be formed both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Peptide" and "polypeptide" as used herein, and unless otherwise specified, refer to polymer compounds of two or more amino acids joined through the main chain by peptide amide bonds (—C(O)NH—). The term "peptide" typically refers to short amino acid polymers (e.g., chains having fewer than 25 amino acids), whereas the term "polypeptide" typically refers to longer amino acid polymers (e.g., chains having more than 25 amino acids).

As used herein, "protein biologics" refer to protein- or peptide-based products produced by recombinant DNA technology and can include, for example, protein therapeutics, tissue (including blood) protein factors (e.g., factor VIII, thrombolytic agents, hormones, growth factors, interferons and enzymes), vaccines, monoclonal antibodies, and receptor molecules.

As used herein, a "protein of interest" or "POI" describes any protein, or functional fragment (such as a protein domain) or derivative thereof, that one skilled in the art wishes to study.

As used herein, the terms "domain" and "region" are used interchangeably herein and refer to a contiguous sequence of amino acids within a protein, typically characterized by being either conserved or variable and having a defined function, such as ligand binding, conferring stability or instability, enzymatic function, etc.

As used herein, "conservative amino acid substitutions" are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution since both are similarly-sized negatively-charged amino acids. Groupings of amino acids by physico-chemical properties are known to those of skill in the art.

As used herein, a "variant" protein is a protein having an amino acid sequence that may or may not occur in nature, as exemplified by sequences in GenBank. As used herein, a "mutant" is a mutated protein that may occur in nature, or may be designed or engineered such that its properties (e.g., stability) or functions (e.g., ligand binding) are altered. "Variant" as used herein also describes a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid (e.g., replacing an amino acid with a different amino acid of similar properties, such as hydrophilicity, degree, and distribution of charged regions) is recognized in the art as typically involving a minor change. These minor changes can be identified, in part, by considering the hydropathic index of amino acids, as understood in the art. The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Sequence identity" refers to the degree two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

"Subject" and "patient" as used herein interchangeably refers to any vertebrate, including, but not limited to, a mammal and a human. In some embodiments, the subject may be a human or a non-human. The subject or patient may be undergoing forms of treatment. "Mammal" as used herein refers to any member of the class Mammalia, including, without limitation, humans and nonhuman primates such as chimpanzees and other apes and monkey species; farm animals such as cattle, sheep, pigs, goats, llamas, camels, and horses; domestic mammals such as dogs and cats; laboratory animals including rodents such as mice, rats, rabbits, guinea pigs, and the like. The term does not denote a particular age or sex. Thus, adult and newborn subjects, as well as fetuses, whether male or female, are intended to be included within the scope of this term.

"Subsequence" refers to peptide or polypeptide that has 100% sequence identify with another, larger peptide or polypeptide. The subsequence is a perfect sequence match for a portion of the larger amino acid chain.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Epitope Screening

The present disclosure includes materials and methods related to the expression of epitopes using a cell-free protein synthesis (CFPS) platform and a protein expression cassette, such as the concatenated epitope cassettes provided herein, to perform a screen to identify immunogenic epitopes. In some embodiments, the systems and methods of the present disclosure facilitate the expression of concatenated epitopes for rapid epitope screening and for the synthesis of novel vaccines containing multiple epitopes from different proteins, multiple epitopes from the same protein, multiple epitopes from the same organism, and/or custom vaccines containing multiple epitopes from different organisms. In accordance with these embodiments, the systems and methods described herein can be used to generate at least one epitope of at least one antigen derived from a pathogen. Pathogens which may be targeted by the subject vaccines include, but are not limited to infectious virus, infectious bacteria, infectious parasites and infectious fungi. In some embodiments, polytope vaccines are provided comprising a plurality of epitopes from one or more such antigens (e.g., multi-epitope vaccines). In some embodiments, the systems and methods described herein can be used to generate at least one epitope derived from at least one antigen associated with cancer. The epitopes can be derived from known cancerous antigens, and/or antigens predicted to be associated with one or more aspects of cancer. As would be appreciated by one of ordinary skill in the art, the systems and methods of the present disclosure can be used to facilitate the expression of any concatenated epitopes, known or not yet identified (e.g., candidate epitopes), such as for the purpose of performing an epitope screen and/or generating a vaccine composition.

In accordance with these embodiments, a protein expression cassette can include two or more concatenated epitopes. In some embodiments, the two or more concatenated epitopes comprise the polypeptide of SEQ ID NO: 1. In some embodiments, the two or more concatenated epitopes comprise the polypeptide of SEQ ID NO: 9. In other embodiments, the two or more concatenated epitopes comprise the polypeptide of SEQ ID NO: 17. In other embodiments, the two or more concatenated epitopes comprise the polypeptide of SEQ ID NO: 25. In other embodiments, the two or more concatenated epitopes comprise the polypeptide of SEQ ID NO: 34.

In some embodiments, the two or more concatenated epitopes comprise a polypeptide having a sequence that is about 50% identical to SEQ ID NOs: 1, 9, 17, 25, or 34. In some embodiments, the two or more concatenated epitopes comprise a polypeptide having a sequence that is about 60% identical to SEQ ID NOs: 1, 9, 17, 25, or 34. In some embodiments, the two or more concatenated epitopes comprise a polypeptide having a sequence that is about 70% identical to SEQ ID NOs: 1, 9, 17, 25, or 34. In some embodiments, the two or more concatenated epitopes comprise a polypeptide having a sequence that is about 80% identical to SEQ ID NOs: 1, 9, 17, 25, or 34. In some embodiments, the two or more concatenated epitopes comprise a polypeptide having a sequence that is about 85% identical to SEQ ID NOs: 1, 9, 17, 25, or 34. In some embodiments, the two or more concatenated epitopes comprise a polypeptide having a sequence that is about 90% identical to SEQ ID NOs: 1, 9, 17, 25, or 34. And in some embodiments, the two or more concatenated epitopes comprise a polypeptide having a sequence that is about 95% identical to SEQ ID NOs: 1, 9, 17, 25, or 34.

In some embodiments, epitopes generated using the systems and methods described herein can be immobilized on or attached to a substrate to facilitate a screen whereby candidate immunogenic epitopes that bind an antibody can be identified. The methods can include providing a substrate (e.g., a solid support) capable of binding candidate epitopes, including, in some cases, through the use of a peptide tag. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, and a variety of other polymers. The support may take on a variety of geometries, including the use of beads (e.g., affinity chromatography columns), magnetic beads, microtiter plates, and the like. In accordance with these embodiments, various screening methodologies can be used, including but not limited to, antibody-based methodologies such as Western blotting and ELISAs.

Antibody binding to a candidate epitope can be evaluated using various means known in the art, including but not limited to chemiluminescence, fluorescence, and enzyme-based methods, and may include the use of peptide tags. The term "antibody" includes antibody fragments, as are known in the art, Including Fab Fab$_2$, single chain antibodies (scFv or Fv for example), chimeric antibodies, and the like, either produced by the modification of whole antibodies or those synthesized de novo using recombinant DNA technologies. The term "antibody" further comprises polyclonal antibodies and monoclonal antibodies, which can be agonist or antagonist antibodies. The antibodies may be polyclonal or monoclonal. In addition, it may be desirable to utilize a mixture of antibodies which bind to different discontinuous epitopes in order to elucidate more than one of the localized tertiary structures of the target protein. That is, in some cases, it may be preferable to map the active site of the target protein, including enzymatic activity, binding activity, activation activity, and the like, and thus choose antibodies that reduce or eliminate the biological function of the target protein.

Other means for performing an epitope screen and/or evaluating immunogenicity of a candidate epitope are well known in the art (see, e.g., Epitope Mapping Protocols in Methods in Molecular Biology, Vol. 66, G. E. Morris, Ed. (1996)).

3. Vaccines

The present disclosure includes materials and methods related to the expression of epitopes using a cell-free protein synthesis (CFPS) platform and a protein expression cassette, such as the concatenated epitope cassettes provided herein, for the generation of multi-epitope vaccines or other compositions capable of generating an immune response. In some embodiments, the systems and methods of the present disclosure facilitate the expression of concatenated epitopes (e.g., epitopes identified using reverse vaccinology approaches) for rapid epitope screening as well as synthesis of novel vaccines containing multiple epitopes from different proteins, multiple epitopes from the same protein, multiple epitopes from the same organism, or custom vaccines containing multiple epitopes from different organisms.

In accordance with these embodiments, a protein expression cassette can include two or more concatenated epitopes. In some embodiments, the two or more concatenated epitopes comprise the polypeptide of SEQ ID NO: 1. In some embodiments, the two or more concatenated epitopes comprise the polypeptide of SEQ ID NO: 9. In other embodiments, the two or more concatenated epitopes comprise the polypeptide of SEQ ID NO: 17. In other embodiments, the two or more concatenated epitopes comprise the polypeptide of SEQ ID NO: 25. In other embodiments, the two or more concatenated epitopes comprise the polypeptide of SEQ ID NO: 34.

In some embodiments, the two or more concatenated epitopes comprise a polypeptide having a sequence that is about 50% identical to SEQ ID NOs: 1, 9, 17, 25, or 34. In some embodiments, the two or more concatenated epitopes comprise a polypeptide having a sequence that is about 60% identical to SEQ ID NOs: 1, 9, 17, 25, or 34. In some embodiments, the two or more concatenated epitopes comprise a polypeptide having a sequence that is about 70% identical to SEQ ID NOs: 1, 9, 17, 25, or 34. In some embodiments, the two or more concatenated epitopes comprise a polypeptide having a sequence that is about 80% identical to SEQ ID NOs: 1, 9, 17, 25, or 34. In some embodiments, the two or more concatenated epitopes comprise a polypeptide having a sequence that is about 85% identical to SEQ ID NOs: 1, 9, 17, 25, or 34. In some embodiments, the two or more concatenated epitopes comprise a polypeptide having a sequence that is about 90% identical to SEQ ID NOs: 1, 9, 17, 25, or 34. And in some embodiments, the two or more concatenated epitopes comprise a polypeptide having a sequence that is about 95% identical to SEQ ID NOs: 1, 9, 17, 25, or 34.

In some embodiments, epitopes generated using the systems and methods described herein can be used to generate a vaccine. Such vaccines include, but are not limited to, conventional types of vaccines such as modified live vaccines, attenuated vaccines, inactivated vaccines, subunit vaccines, and recombinant type vaccines such as vaccines in which one or more protective antigens from a pathogenic organism are produced and are used in crude or purified form, or recombinant vaccines in which one or more protective antigens are carried by a live vector such as another live or modified live bacteria, a live or modified live virus, a live prokaryotic cell or some other type of live organism.

In some embodiments, epitopes generated using the systems and methods described herein can be used to generate at least one epitope of at least one antigen derived from a pathogen. Pathogens which may be targeted by the subject vaccines include, but are not limited to infectious virus, infectious bacteria, infectious parasites and infectious fungi. In some embodiments, polytope vaccines are provided comprising a plurality of epitopes from one or more such antigens (e.g., multi-epitope vaccines). Microbial antigens used may be inherently immunogenic, or non-immunogenic, or slightly immunogenic. Exemplary antigens include, but are not limited to, synthetic, recombinant, foreign, or homologous antigens, and antigenic materials may include but are not limited to proteins, peptides, polypeptides, lipids, glycolipids, carbohydrates and DNA.

In some embodiments, the two or more concatenated epitopes comprise any combination of SEQ ID NOs: 2-8, 10-16, 18-24, 26-33, and 35-41. As would be recognized by one of ordinary skill in the art based on the present disclosure, the polypeptides of SEQ ID NOs: 2-8, 10-16, 18-24, 26-33, and 35-41 can be arranged in various combinations to generate multi-epitope vaccines or other compositions capable of generating an immune response.

Exemplary viral pathogens include, but are not limited to, infectious virus that infect mammals, and more particularly humans. Examples of infectious virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus).

Also, gram negative and gram positive bacteria may be targeted by vaccines developed using the methods described herein, and can include, but are not limited to *Pasteurella* species, *Staphylococci* species, and *Streptococcus* species. Gram negative bacteria include, but are not limited to, *Escherichia coli, Pseudomonas* species, and *Salmonella* species. Specific examples of infectious bacteria include but are not limited to: *Helicobacterpyloris, Borelia burgdorferi, Legionella pneumophilia, Mycobacteria* sps (e.g., *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes,* (Group A *Streptococcus), Streptococcus agalactiae* (Group B *Streptococcus), Streptococcus (viridans* group), *Streptococcusfaecalis, Streptococcus bovis, Streptococcus* (anaerobic sps.), *Streptococcus pneumoniae,* pathogenic *Campylobacter* sp., *Enterococcus* sp., *Haemophilus infuenzae, Bacillus antracis, Corynebacterium diphtheriae, Corynebacterium* sp., *Erysipelothrix rhusiopathiae, Clostridium perfringens, Clostridium tetani, Enterobacter aerogenes, Kiebsiella pneumoniae, Pasteurella multocida, Bacteroides* sp., *Fusobacterium nucleatum, Streptobacillus moniliformis, Treponema pallidium, Treponema pertenue, Leptospira, Rickettsia,* and *Actinomyces israelli.*

Polypeptides of bacterial pathogens which may find use as sources of microbial antigens according to embodiments of the present include, but are not limited to, an iron-regulated outer membrane protein, ("IROMP"), an outer membrane protein ("OMP"), and an A-protein of *Aeromonis salmoni-* cida which causes furunculosis, p57 protein of *Renibacterium salmoninarum* which causes bacterial kidney disease ("BKD"), major surface associated antigen ("msa"), a surface expressed cytotoxin ("mpr"), a surface expressed hemolysin ("ish"), and a flagellar antigen of Yersiniosis; an extracellular protein ("ECP"), an iron-regulated outer membrane protein ("IROMP"), and a structural protein of *Pasteurellosis*; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of *Ichthyophthirius*; and a structural and regulatory protein of *Cytophaga columnari*; and a structural and regulatory protein of *Rickettsia*.

Examples of pathogens further include, but are not limited to, infectious fungi that infect mammals, and more particularly humans. Examples of infectious fungi include, but are not limited to: *Cryptococcus neoformans, Histoplasma capsulatum, Coccidioides immitis, Blastomyces dermatitidis, Chlamydia trachomatis, Candida albicans*. Examples of infectious parasites include *Plasmodium* such as *Plasmodium falciparum, Plasmodium malariae, Plasmodium ovale*, and *Plasmodium vivax*. Other infectious organisms (e.g., protists) include *Toxoplasma gondii*. Polypeptides of a parasitic pathogen include but are not limited to the surface antigens of *Ichthyophthirius*.

Exemplary non-human pathogens include, but are not limited to, mouse mammary tumor virus ("MMTV"), Rous sarcoma virus ("RSV"), avian leukemia virus ("ALV"), avian myeloblastosis virus ("AMV"), murine leukemia virus ("MLV"), feline leukemia virus ("FeLV"), murine sarcoma virus ("MSV"), gibbon ape leukemia virus ("GALV"), spleen necrosis virus ("SNV"), reticuloendotheliosis virus ("RV"), simian sarcoma virus ("SSV"), Mason-Pfizer monkey virus ("MPMV"), simian retrovirus type 1 ("SRV-1"), lentiviruses such as HIV-1, HIV-2, SIV, Visna virus, feline immunodeficiency virus ("FIV"), and equine infectious anemia virus ("EIAV"), T-cell leukemia viruses such as HTLV-1, HTLV-II, simian T-cell leukemia virus ("STLV"), and bovine leukemia virus ("BLV"), and foamy viruses such as human foamy virus ("HFV"), simian foamy virus ("SFV") and bovine foamy virus ("BFV").

4. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

To facilitate screening, predicted epitopes were concatenated for synthesis as gene blocks, each one containing combinations of the various candidate epitopes. As depicted in FIG. 1, each gene block contained a T7 promoter, a signal peptide sequence and FLAG-tag at its N-terminus, and a His-tag at the C-terminus; the latter was included to enable antigenicity screening by allowing immobilization of candidate peptides on nickel-coated plates while the FLAG-tag provides a means to determine the relative expression levels of epitope concatemers. Individual epitopes were linked together using 6 amino acid spacers (3 amino acids flanking each epitope on both sides). In the sequences below, the predicted B-cell epitope sequences are indicated as bolded text with the flanking sequences not bolded. Predicted, promiscuous T-cell epitopes that overlap these potential B-cell epitopes are further indicated as underlined text.

Concatenated FnbPA 1-7. For a schematic of concatenated FnbA 1-7 see FIG. 1. Predicted amino acids sequence of concatenated FnbA 1-7 (232 aa's; predicted to be 25.2 kD MW when fused to an N-terminal signal peptide/FLAG tag, and C-terminal His tag).

```
                                             (SEQ ID NO: 1)
SVFLGTMIVVGMGQDKEAAASEQKTTLKRGDYFDFTLSNNVNTYGVSTAR

AIDGEGGYVDGYIETIEETDSSAIDIHSGLGTENGHGNYGVIEEIEENSH

VDIKKYEQGGNIVDIDFDSVPQIQGQNNGNKYEQGGNIIDIDFDSVPQIH

GFNKHTGGHNSVDFEEDTLPKVSGQNEGQQTI
```

Individual epitope sequences are shown below:

FnbA.1 (SEQ ID NO: 2): SVFLGTMIVVGMGQDKEAAASEQKTT

FnbA.2 (SEQ ID NO: 3): LKRGDYFDFTLSNNVNTYGVSTAR

FnbA.3 (SEQ ID NO: 4): AIDGEGGYVDGYIETIEETDSSAIDI

FnbA.4 (SEQ ID NO: 5): GLGTENGHGNYGVIEEIEENSHVDIK

FnbA.5 (SEQ ID NO: 6): KYEQGGNIVDIDFDSVPQIQGQNNGN

FnbA.6 (SEQ ID NO: 7): KYEQGGNIIDIDFDSVPQIHGFNKHT

FnbA.7 (SEQ ID NO: 8): GGHNSVDFEEDTLPKVSGQNEGQQTI

Concatenated FnbPB 1-8. For a schematic of concatenated FnbPB 1-8 see FIG. 1. Predicted amino acids sequence of concatenated FnbB 1-8 (256 aa's; predicted to be 28.4 kD MW when fused to an N-terminal signal peptide/FLAG tag, and C-terminal His tag).

```
                                             (SEQ ID NO: 9)
SVFLGTMIVVGMGQEKEAAASEQNNTIKPGDYFDFTLSNNVETHGISPLR

SEPIELDIKSEPPVEKHELTGTIEESNDSKPIDFEYHTAVEGVEGHAEGL

GTENGHGNYGVIEEIEENSHVDIKEEDKPKYEQGGNIVDIDFDSVPQIHG

QNKGDYEHGGNIIDIDFDSVPHIHGFNKHTGGHNSVDFEEDTLPQVSGHN

EGQQTI
```

Individual epitope sequences are shown below:

FnbB.1 (SEQ ID NO: 10): SVFLGTMIVVGMGQEKEAAASEQNNT

FnbB.2 (SEQ ID NO: 11): IKPGDYFDFTLSNNVETHGISPLR

FnbB.3 and 4 (SEQ ID NO: 12): SEPIELDIKSEPPVEKHELT
GTIEESNDSKPIDFEYHTAVEGVEGHAE FnbB.5 (SEQ ID NO: 13): GLGTENGHGNYGVIEEIEENSHVDIK FnbB.6 (SEQ ID NO: 14): EEDKPKYEQGGNIVDIDFDSVPQIHG

QNKGD

FnbB.7 (SEQ ID NO: 15): YEHGGNIIDIDFDSVPHIHGFNKHT

FnbB.8 (SEQ ID NO: 16): GGHNSVDFEEDTLPQVSGHNEGQQTI

Concatenated Epitopes Mix 2. For a schematic of concatenated Epitopes Mix 2 see FIG. 1. Predicted amino acids sequence of Concatenated ClfA and B Epitopes (232 aa's; predicted to be 25.6 kD MW when fused to an N-terminal signal peptide/FLAG tag, and C-terminal His tag).

(SEQ ID NO: 17)
TNQLTNVTVGIDSGDTVYPHQAGYVKGVIDSDGNVIYTFTDYVDTKENVT

ANITMPAYIDPENVTKTGNVTLTTGIGSNFEDVTNSVNITFPNPNQYKVE

FNTPTLDLPQSSPQTISNAQGTSKPSVRTRAKD**FQLEKTTFDPNQSGNTF

MAANFTFSLPLFTDRAKAPKSGTYDANINIAD

Epitopes include ClfA.1, ClfA.2, ClfA.3, and ClfA.4 from the Clumping Factor A Protein, and ClfB.1, ClfB.2, and ClfB.3 from the Clumping Factor B Protein.

Individual epitope sequences are shown below:

ClfA.1 (SEQ ID NO: 18): TNQLTNVTVGIDSGDTVYPHQAGYVK

ClfA.2 (SEQ ID NO: 19): GVIDSDGNVIYTFTDYVDTKENVTAN

ClfA.3 (SEQ ID NO: 20): ITMPAYIDPENVTKTGNVTLTTGIGS

ClfA.4 (SEQ ID NO: 21): NFED**VTNSVNITFPNPNQYKVEFNTP

ClfB.1 (SEQ ID NO: 22): TLDLPQSSPQTISNAQGTSKPSVRT

R

ClfB.2 (SEQ ID NO: 23): AKDFQLEKTTFDPNQSGNTFMAANF

T

ClfB.3 (SEQ ID NO: 24): FSL**PLFTDRAKAPKSGTYDANINIA

D

Concatenated SraP1-8. For a schematic of concatenated SraP1-8 see FIG. 1. Predicted amino acids sequence of concatenated SraP1-8 (275 aa's; predicted to be 28.kD MW when fused to an N-terminal signal peptide/FLAG tag, and C-terminal His tag).

(SEQ ID NO: 25)
LTSELNTQSETVGNQNSTTIEASTSTW**IAKSGTTNFSLSMTASTGGATNL

QQVTGLPSGLTFDSTNNTISGTPTNIGTVSLSDSVSASKS**LSTSESNSVS

SSTSTSLVNSQSVSSSMSDSGSQSMSDSVSTSDSSSLSVSTSLRSSAS**ES

DSMSTSDSSSISGSNSTSTSLSTISISGSQSTVESESTSDSTSISDSESS

ESVSTSTSTSLSTSDSTSTSESLST

Individual epitope sequences are shown below:

SraP.1 (SEQ ID NO: 26): LTSELNTQSETVGNQNSTTIEASTST

SraP.2 (SEQ ID NO: 27): WIAKSGTTNFSLSMTASTGGATNLQQ

SraP.3 (SEQ ID NO: 28): VTGLPSGLTFDSTNNTISGTPTNIGT

SraP.4 (SEQ ID NO: 29): VSLSDSVSASKS**LSTSESNSVSSSTS

TSLVNSQSVSSSMSD

SraP.5 (SEQ ID NO: 30): SGSQSMSDSVSTSDSSSLSVSTSLRS

SraP.6 (SEQ ID NO: 31): SASESDSMSTSDSSSISGSNSTSTSL

ST

SraP.7 (SEQ ID NO: 32): ISISGSQST**VESESTSDSTSISDSES

SraP.8 (SEQ ID NO: 33): SESVSTSTSTSLSTSDSTSTSESLST

Concatenated Epitopes Mix 1. For a schematic of concatenated Epitopes Mix 1 see FIG. 1. Predicted amino acids sequence of concatenated Epitopes Mix 1 (243 aa's; predicted to be 27.1 kD MW when fused to an N-terminal signal peptide/FLAG tag, and C-terminal His tag).

(SEQ ID NO: 34)
PQGYGSYNSFSINYKTKITNEQQKEFNKNA**FAMDKSHPEPIEDNDKHETI

KELTIAAIGITTTTIASTADASEGYGPREKKPVSINHNIDYNI**LEFNDGT

FEYGARPQFNKPAAKVPSGASTGEHEAVELRDGDKSRYLGKKRG**LETAVG

DEGGFAPKFEGTEDAVEEFYENGVYDYSKFEGEHGAKRTA**AEQ

Individual epitope sequences are shown below:

Cna.1 (SEQ ID NO: 35): PQGYGSYNSFSINYKTKITNEQQKEF

EbpS.1 (SEQ ID NO: 36): NKNA**FAMDKSHPEPIEDNDKHETIKE

Efb.1 (SEQ ID NO: 37): LTIAA**IGITTTTIASTADASEGYGPRE

KKPVS**INHNI

Efb.2 (SEQ ID NO: 38): DYNILEFNDGTFEYGARPQFNKPAAK

Eno.1 (SEQ ID NO: 39): VPSGASTGEHEAVELRDGDKSRYLGK

Eno.2 (SEQ ID NO: 40): KRGLETAVGDEGGFAPKFEGTEDAVE

Eno.3 (SEQ ID NO: 41): EFYENGVYDYSKFEGEHGAKRTAAEQ

Example 2

Figure 2A:
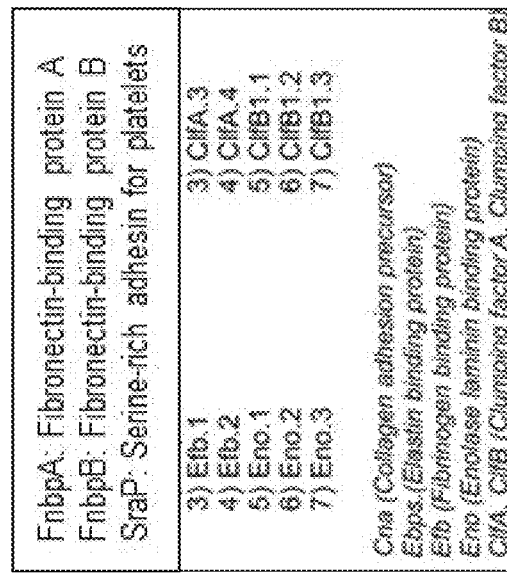
FIGS. 2A-2B include representative results demonstrating cell-free expression of epitope concatemers.
Figure 2B:
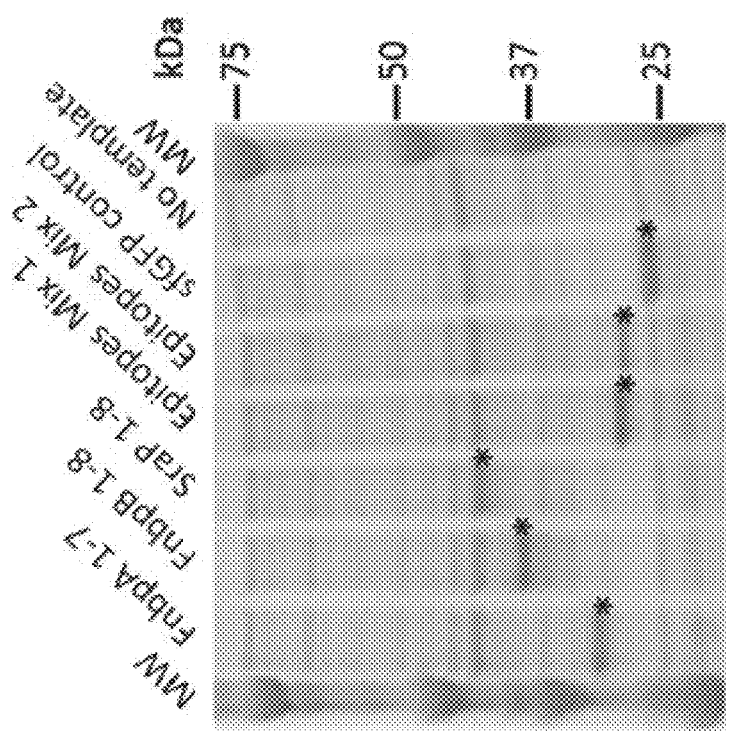

FIGS. 2A-2B includes representative results demonstrating cell-free expression of epitope concatemers. As shown in FIG. 2A, polyacrylamide gel analyses was performed with five epitope concatemers expressed in an *E. coli* cell-free expression system. Plasmid templates that encoded for the epitope concatemers were fused to an N-terminal signal peptide/FLAG tag, and C-terminal His tags were included in in vitro transcription-translation reactions. Products were size fractionated on 4-12% SDS-PAGE gels in MOPS Buffer, followed by protein visualization by COOMASIE BLUE staining. A positive control plasmid template (super folder GFP, sfGFP) and a no template reaction were also included. In vitro expressed products are indicated with an asterisk. Quantification against a BSA standard curve indicate expression levels between 1-2 mg/ml for the epitope concatemers (not shown). FIG. 2B summarizes the epitope compositions of Epitope Mix 1 and Epitopes Mix 2 concatemers.

Example 3

Figure 3:
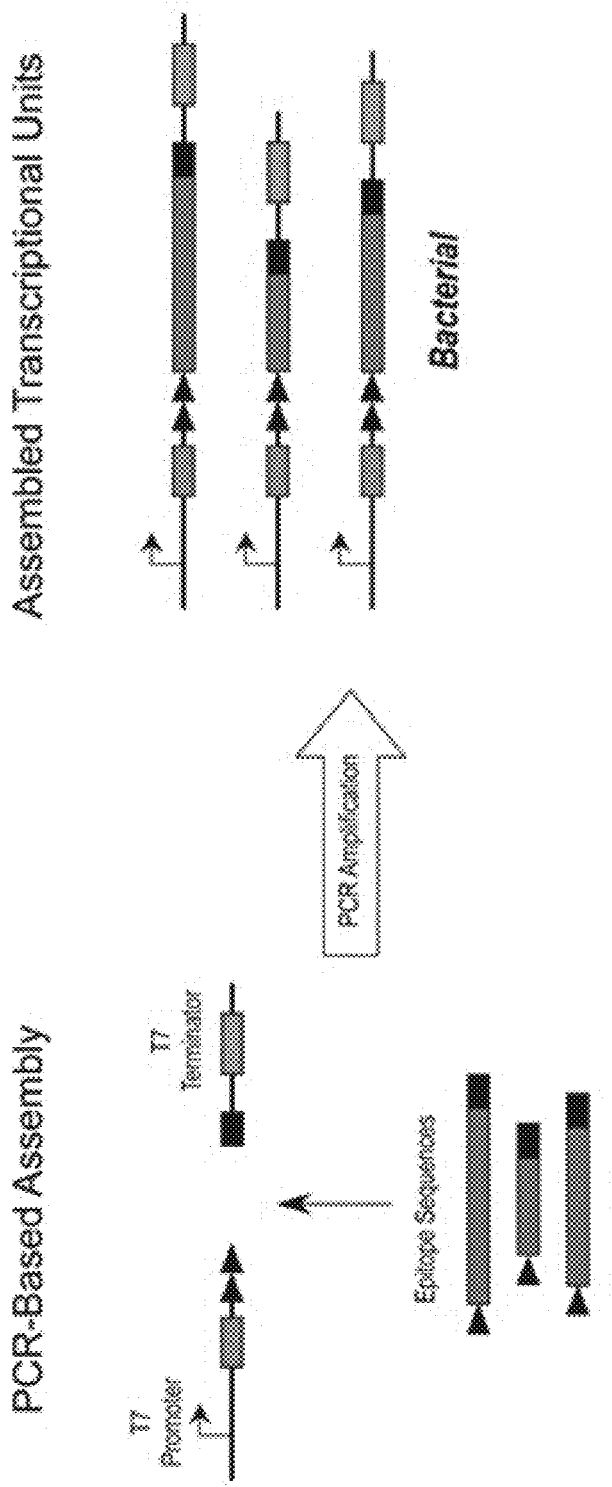
FIG. 3 includes a schematic representation of a rapid and flexible assembly approach for the generation of linear DNA templates for cell-free expression.

FIG. 3 includes a schematic representation of a rapid and flexible assembly approach for the generation of linear DNA templates for cell-free expression. Linear DNA templates were generated for expression in a bacterial cell-free system using a PCR-based approach that utilizes common PCR products: a 5' product that includes a T7 transcriptional promoter, the engineered signal peptide and FLAG tag, and a 3' product that includes a T7 Terminator sequence. Individual epitope sequences were generated by PCR containing 5' and 3' regions that overlap the common PCR products. Full transcriptional units were assembled by allowing the three sets of fragments to self-anneal and extend using a DNA polymerase, followed by PCR amplification using primers that anneal to the extreme ends of the assembled products. The system is flexible in that the test sequences may be individual epitopes or epitope concatemers, and the common 5' and 3' products may contain other elements such as IRES sequences, or poly(A) stretches that enable expression in cell free-systems from other organisms such as a mammalian cell-free lysate prepared from (e.g., CHO cells). The rapid and flexible nature of this template assembly approach enables high throughput expression of peptides/proteins for downstream testing or analyses.

Example 4

Figure 4:
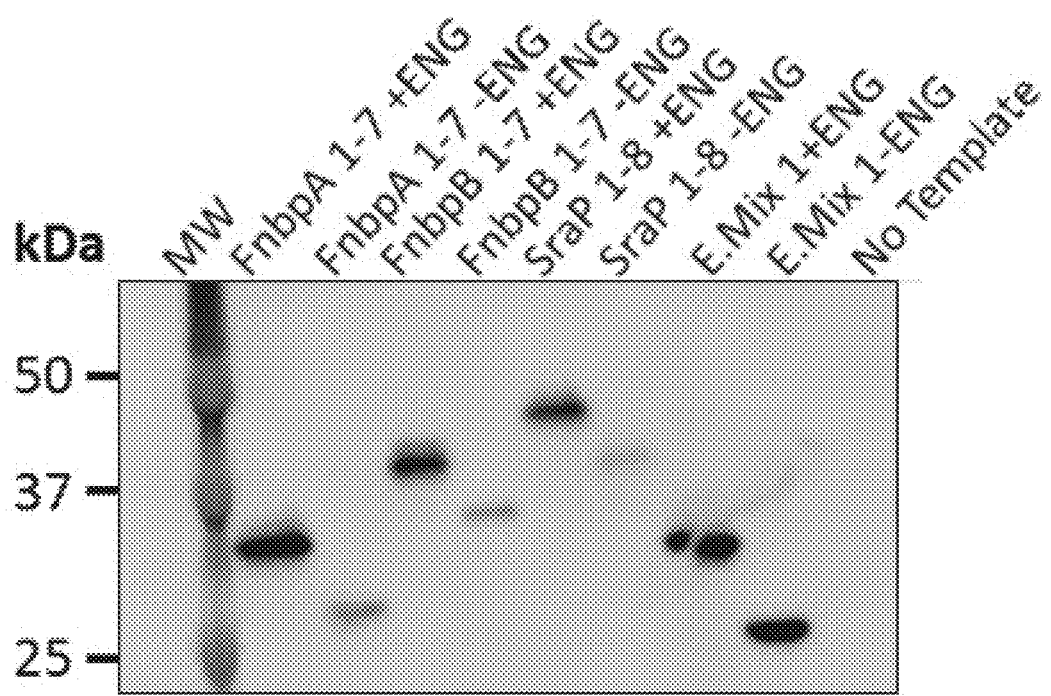
FIG. 4 includes representative results of the use of an engineered leader sequence to enhance expression of epitope concatemers in a cell-free system.

FIG. 4 includes representative results of the use of an engineered leader sequence to enhance expression of epitope concatemers in a cell-free system. Western Blot analyses were performed on epitope concatemers expressed in a bacterial cell-free system. Each concatemer was expressed from linear DNA templates that contained (+ENG) or lacked (−ENG) the engineered mRNA leader sequence that encode for the signal peptide and FLAG tag. The expression level of the cell-free products were evaluated using an antibody to the C-terminal His tag present in each concatemer. The analyses shows that the inclusion of the engineered sequences results in an increase in concatemers expression relative to a concatemers that lacks the sequence. The molecular weights of cell-free products that lack the engineered sequence are less than that of the molecular weights of the products in which it was included.

Figure 5:
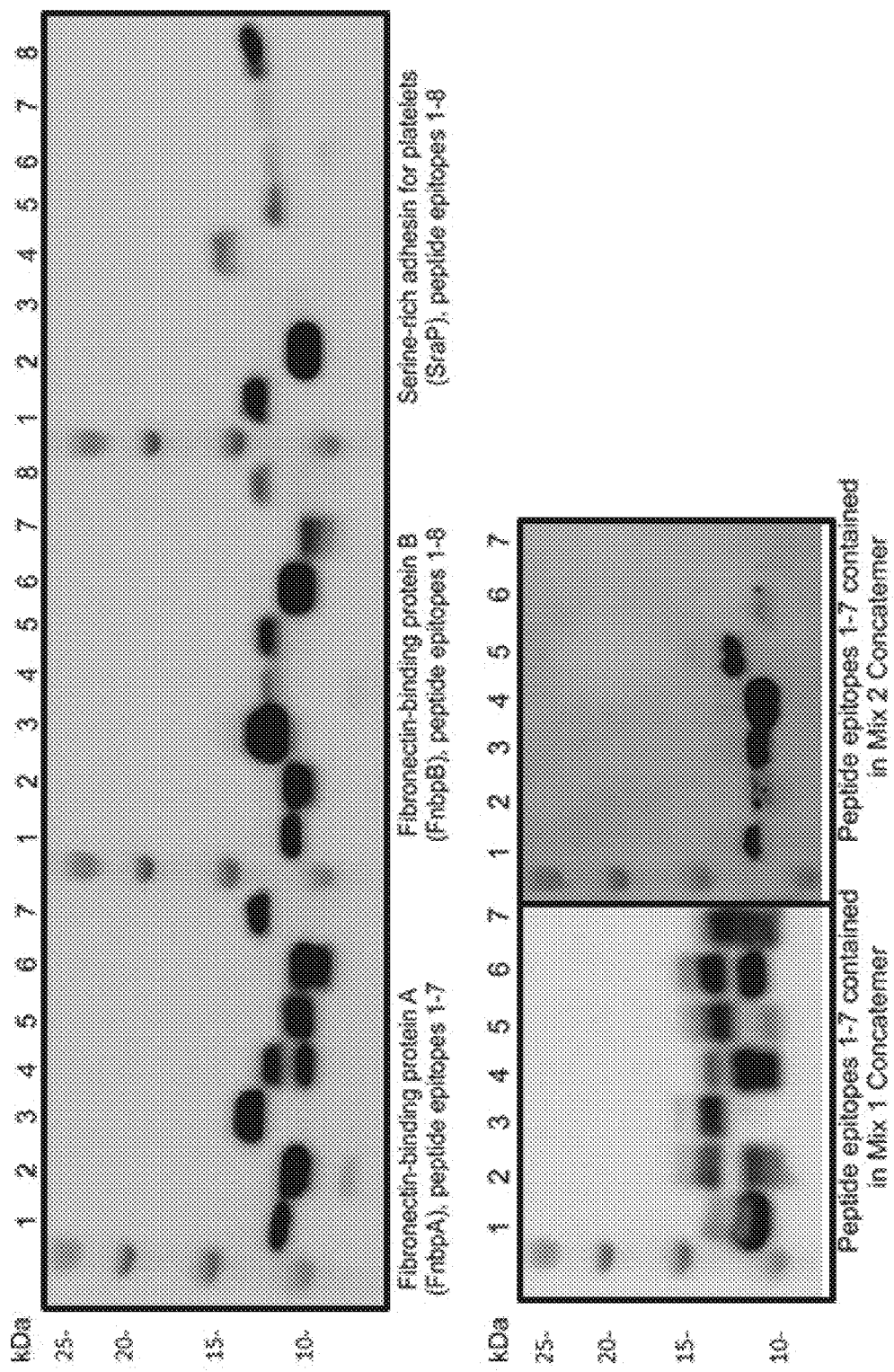
FIG. 5 includes representative results of the expression of individual epitopes using an engineered leader sequence.

FIG. 5 includes representative results of the expression of individual epitopes using an engineered leader sequence. Western Blot analyses were performed on individual epitopes expressed in an E. coli cell-free system. Products were detected using an antibody to the FLAG-tag present at the N-terminus of expressed epitopes. Epitopes were robustly expressed, with detectable expression of 35/37 epitopes that facilitate screening for vaccine development.

Example 5

Figures 6A, 6B, 6C:
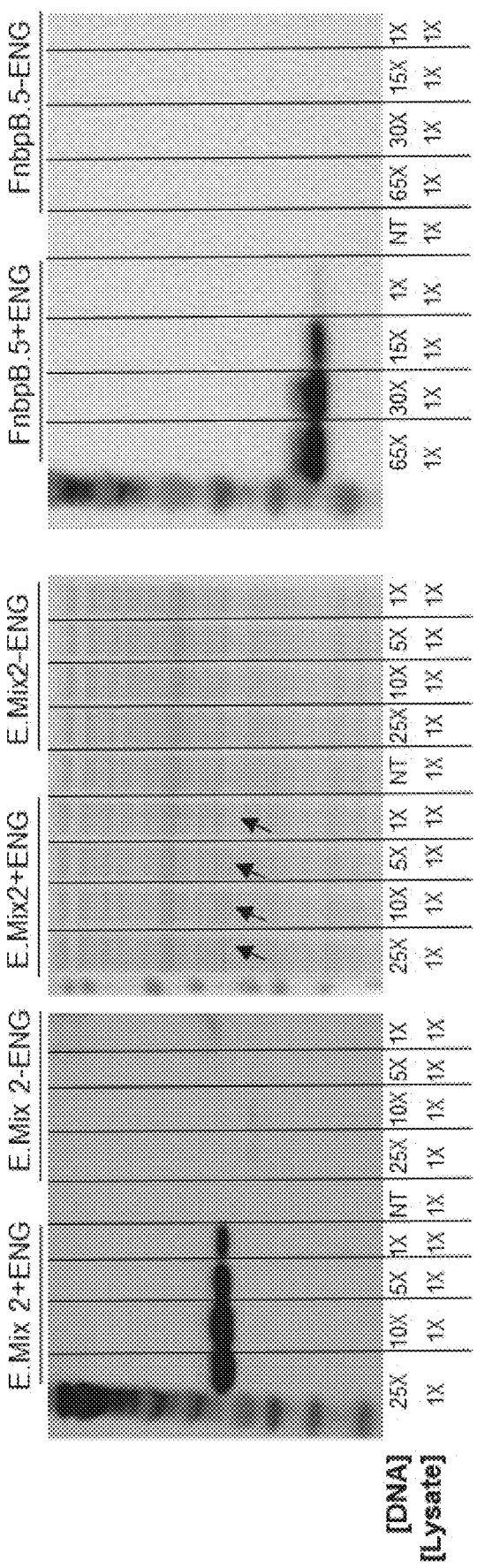
FIGS. 6A-6C include representative results using methods for rapid determination of the optimum DNA concentration for enhanced cell-free protein expression.

FIGS. 6A-6C include representative results using methods for rapid determination of the optimum DNA concentration for enhanced cell-free protein expression. As shown in FIG. 6A, Western Blot analyses were performed with the Epitope Mix 2 concatemer expressed in a bacterial cell-free system. The amount of linear DNA template included in cell-free reactions varied from 1× up to 25× and included (+ENG), or omitted (−ENG) the engineered mRNA leader sequence. The results indicated a dose response with regard to linear DNA template concentration and concatemer expression. Note that expression from the templates that lack the engineered sequences were poorly expressed relative to those that contained it. As shown in FIG. 6B, COOMASIE BLUE stained polyacrylamide gel analyses were performed on the products shown in FIG. 6A. Note that 1/10 of the amount of cell-free reaction volume was analyzed compared with those in FIG. 2. Arrows indicate the stained bands corresponding to the Epitope Mix 2 concatemer. As shown in FIG. 6C, Western Blot analyses was performed on the individual Epitope (FnbPB.5) expressed in a bacterial cell-free system. The amount of linear DNA template included in cell-free reactions varied from 1× up to 65× and included (+ENG), or omitted (−ENG) the engineered mRNA leader sequence. Again, the results indicate a dose response with regard to linear DNA template concentration and epitope expression. Note that expression from the templates that lack the engineered sequences were undetectable relative to those that contained it.

Figure 7:
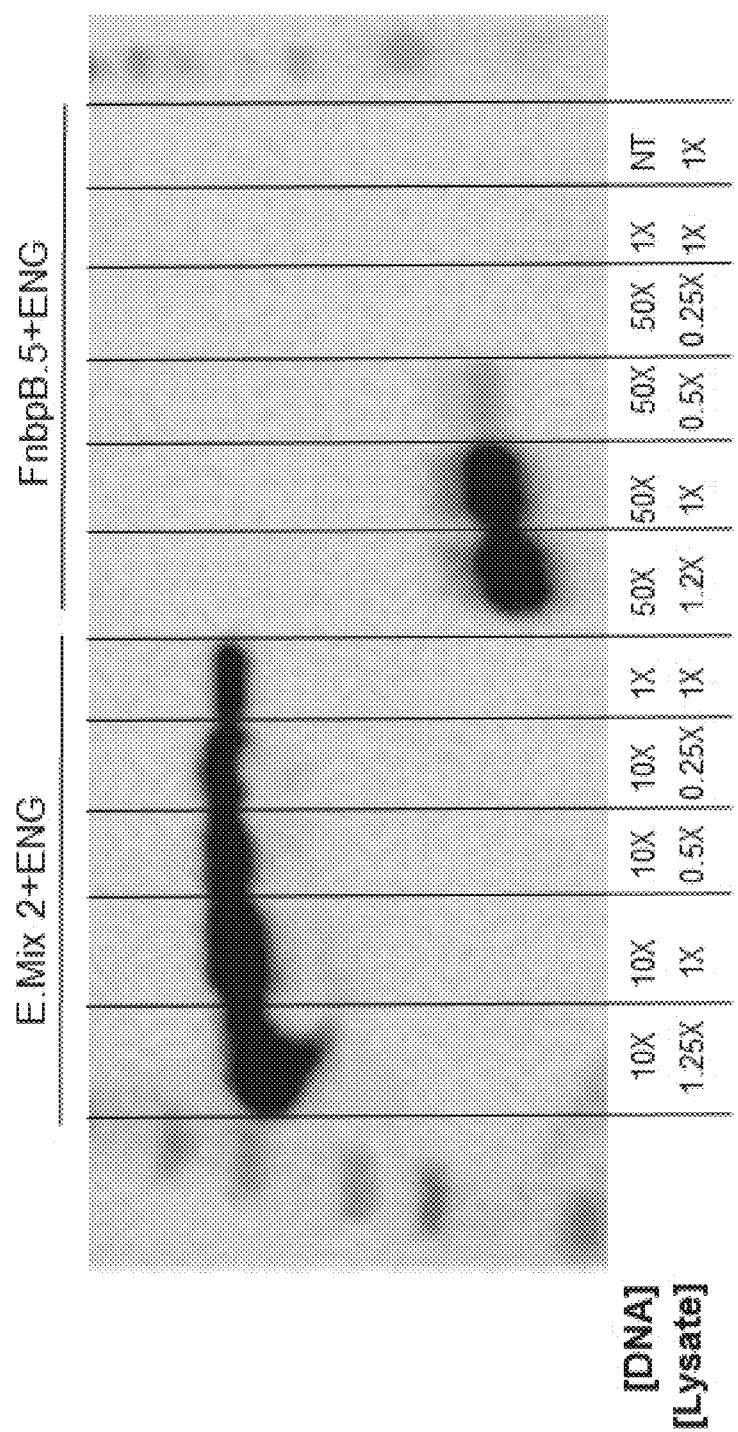
FIG. 7 includes representative results using methods for rapid determination of the optimum lysate concentration for enhanced cell-free protein expression.

FIG. 7 includes representative results using methods for rapid determination of the optimum lysate concentration for enhanced cell-free protein expression. Western Blot analyses were performed with the Epitope Mix 2 concatemer and the individual FnbPB.5 epitope expressed in a bacterial cell-free system. Cell-free reactions were prepared using a concentration of linear DNA template that resulted in the enhanced expression of each peptide (10× for the Epitope mix 2 concatemer, and 50× for the individual FnbPB.5 epitope). The volume of lysate in cell-free reactions was titrated from 1× up to 1.25× and the expression of each epitope candidate protein was compared at each lysate amount, and to that of a standard reaction (1× template and 1× lysate). Note that we observed a dose response to lysate concertation and expression of each type of epitope protein, with the most pronounced benefit observed for the individual epitope.

Example 6

Figure 8:
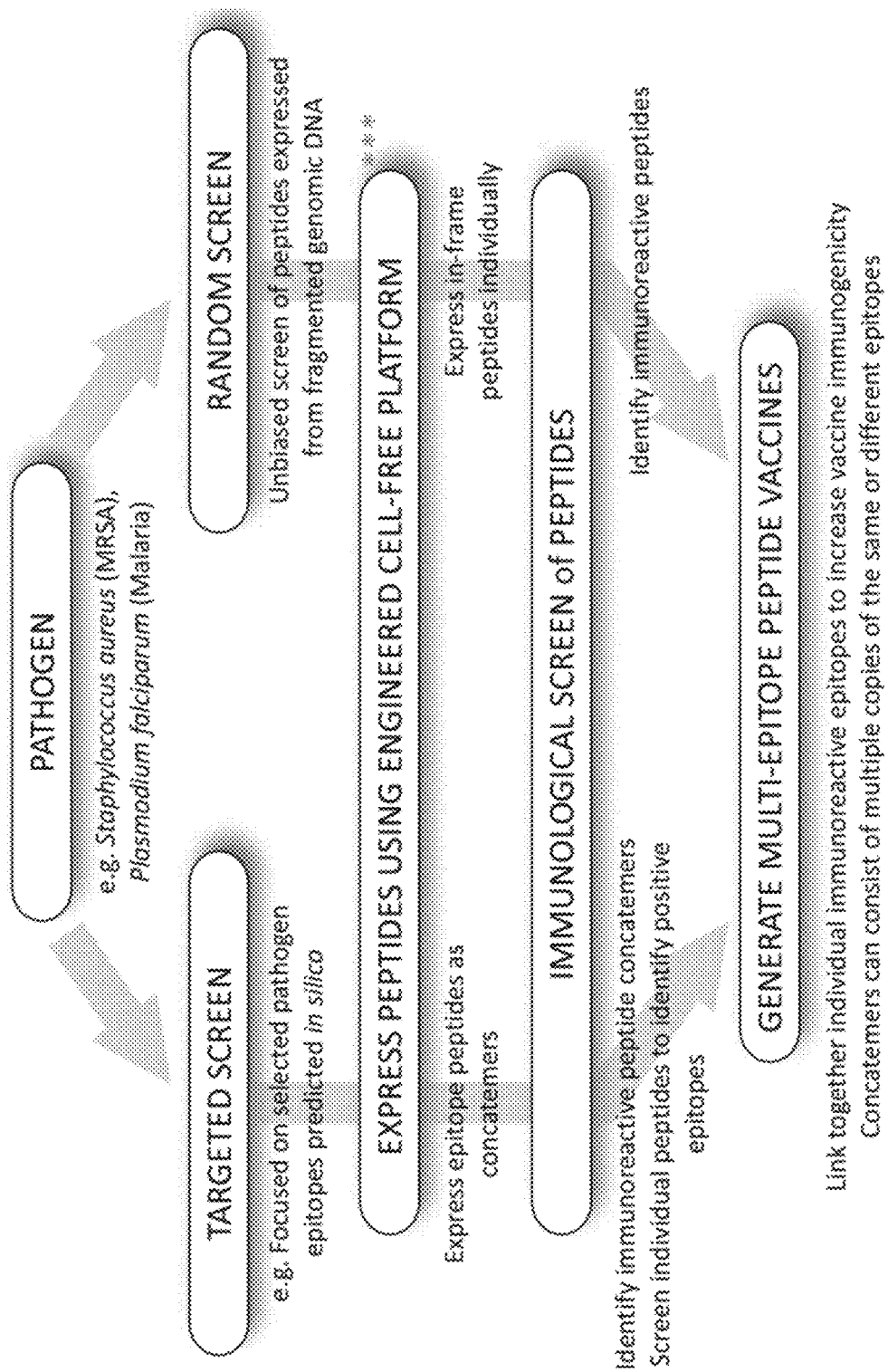
FIG. 8 includes a representative schematic diagram depicting the applications of the optimized cell-free expression platforms provided herein.

FIG. 8 includes a representative schematic diagram depicting the applications of the optimized cell-free expression platforms provided herein. The flow diagram depicts how the optimized expression platform can be utilized to screen candidate epitopes for vaccine development. These approaches can be targeted, in that epitopes predicted in silico are expressed either as concatemers or individually, and subsequently evaluated by immunological approaches to identify immunoreactive peptides, or through unbiased screening of peptides derived from (e.g., fragmented genomic DNA). Identified immunoreactive epitopes can then be used to generate multi-epitope peptide vaccines that may consist of different epitopes from different proteins for a particular pathogen, or multiple copies of the same epitope. Such methods, as described herein, facilitate rapid and efficient epitope screening that has been difficult or impossible to achieve previously due to excessive variability of expression of epitope candidates. Furthermore, multi-epitope peptide vaccines could be designed that incorporate reactive epitopes from multiple pathogens thereby generating broad spectrum peptide vaccines. It should also be noted that the platform described in this document may easily be applied to the screening and identification of peptides beyond vaccines, for example, peptide drugs or antibiotic peptides, as described further herein.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

What is claimed is:

1. A cell-free protein synthesis (CFPS) expression cassette consisting of:
   (a) an isolated concatenated polynucleotide sequence encoding two or more concatenated epitopes as a single fusion peptide, wherein the fusion peptide is fused to an N-terminal signal peptide and wherein the two or more concatenated epitopes consist of different amino acid sequences;
   (b) a heterologous promoter upstream of the sequence encoding the signal peptide;
   (c) a polynucleotide encoding a peptide tag N-terminal to the fusion peptide; and
   (d) a polynucleotide encoding a peptide tag C-terminal to the fusion peptide.

2. The cell-free protein synthesis (CFPS) expression cassette of claim 1, wherein the two or more concatenated epitopes are of a polypeptide having at least 70% sequence identity to the polypeptide of SEQ ID NO: 1.

3. The cell-free protein synthesis (CFPS) expression cassette of claim 1, wherein the two or more concatenated epitopes are of a polypeptide having at least 70% sequence identity to the polypeptide of SEQ ID NO: 9.

4. The cell-free protein synthesis (CFPS) expression cassette of claim 1, wherein the two or more concatenated epitopes are of a polypeptide having at least 70% sequence identity to the polypeptide of SEQ ID NO: 17.

5. The cell-free protein synthesis (CFPS) expression cassette of claim 1, wherein the two or more concatenated epitopes are of a polypeptide having at least 70% sequence identity to the polypeptide of SEQ ID NO: 25.

6. The cell-free protein synthesis (CFPS) expression cassette of claim 1, wherein the two or more concatenated epitopes are of a polypeptide having at least 70% sequence identity to the polypeptide of SEQ ID NO: 34.

7. The cell-free protein synthesis (CFPS) expression cassette of claim 1, wherein the two or more concatenated epitopes are any combination of SEQ ID NOs: 2 to 8.

8. The cell-free protein synthesis (CFPS) expression cassette of claim 1, wherein the two or more concatenated epitopes are any combination of SEQ ID NOs: 10 to 16.

9. The cell-free protein synthesis (CFPS) expression cassette of claim 1, wherein the two or more concatenated epitopes are any combination of SEQ ID NOs: 18 to 24.

10. The cell-free protein synthesis (CFPS) expression cassette of claim 1, wherein the two or more concatenated epitopes are any combination of SEQ ID NOs: 26 to 33.

11. The cell-free protein synthesis (CFPS) expression cassette of claim 1, wherein the two or more concatenated epitopes are any combination of SEQ ID NOs: 2 to 8.

12. The cell-free protein synthesis (CFPS) expression cassette of claim 1, wherein the two or more concatenated epitopes are any combination of SEQ ID NOs: 35 to 41.

13. The cell-free protein synthesis (CFPS) expression cassette of claim 1, wherein the two or more concatenated epitopes are immunogenic epitopes.

14. The cell-free protein synthesis (CFPS) expression cassette of claim 1, wherein the two or more concatenated epitopes are multiple different epitopes from different proteins, the same protein, the same organism, or different organisms.

* * * * *

SEQUENCE LISTING

<160> NUMBER OF SEQ ID NOS: 41

<210> SEQ ID NO 1
<211> LENGTH: 181
<212> TYPE: PRT
<213> ORGANISM: Artificial sequence
<220> FEATURE:
<223> OTHER INFORMATION: Synthetic

<400> SEQUENCE: 1

Ser Val Phe Leu Gly Thr Met Ile Val Val Gly Met Gly Gln Asp Lys
1               5                   10                  15

Glu Ala Ala Ala Ser Glu Gln Lys Thr Thr Leu Lys Arg Gly Asp Tyr
            20                  25                  30

Phe Asp Phe Thr Leu Ser Asn Asn Val Asn Thr Tyr Gly Val Ser Thr
        35                  40                  45

Ala Arg Ala Ile Asp Gly Glu Gly Gly Tyr Val Asp Gly Tyr Ile Glu
    50                  55                  60

Thr Ile Glu Glu Thr Asp Ser Ser Ala Ile Asp Ile His Ser Gly Leu
65                  70                  75                  80

Gly Thr Glu Asn Gly His Gly Asn Tyr Gly Val Ile Glu Glu Ile Glu
                85                  90                  95

Glu Asn Ser His Val Asp Ile Lys Lys Tyr Glu Gln Gly Gly Asn Ile
            100                 105                 110

Val Asp Ile Asp Phe Asp Ser Val Pro Gln Ile Gln Gly Gln Asn Asn
        115                 120                 125

Gly Asn Lys Tyr Glu Gln Gly Gly Asn Ile Ile Asp Ile Asp Phe Asp
    130                 135                 140

Ser Val Pro Gln Ile His Gly Phe Asn Lys His Thr Gly Gly His Asn
145                 150                 155                 160

Ser Val Asp Phe Glu Glu Asp Thr Leu Pro Lys Val Ser Gly Gln Asn
                165                 170                 175

Glu Gly Gln Gln Thr
            180

<210> SEQ ID NO 2
<211> LENGTH: 26
<212> TYPE: PRT
<213> ORGANISM: Artificial sequence
<220> FEATURE:
<223> OTHER INFORMATION: FnbA.1

<400> SEQUENCE: 2

Ser Val Phe Leu Gly Thr Met Ile Val Val Gly Met Gly Gln Asp Lys
1               5                   10                  15

Glu Ala Ala Ala Ser Glu Gln Lys Thr Thr
            20                  25

<210> SEQ ID NO 3
<211> LENGTH: 24
<212> TYPE: PRT
<213> ORGANISM: Artificial sequence
<220> FEATURE:
<223> OTHER INFORMATION: FnbA.2

<400> SEQUENCE: 3

Leu Lys Arg Gly Asp Tyr Phe Asp Phe Thr Leu Ser Asn Asn Val Asn
1               5                   10                  15

Thr Tyr Gly Val Ser Thr Ala Arg
            20

<210> SEQ ID NO 4
<211> LENGTH: 26
<212> TYPE: PRT
<213> ORGANISM: Artificial sequence
<220> FEATURE:
<223> OTHER INFORMATION: FnbA.3

<400> SEQUENCE: 4

Ala Ile Asp Gly Glu Gly Gly Tyr Val Asp Gly Tyr Ile Glu Thr Ile
1               5                   10                  15

Glu Glu Thr Asp Ser Ser Ala Ile Asp Ile
            20                  25

<210> SEQ ID NO 5
<211> LENGTH: 26
<212> TYPE: PRT
<213> ORGANISM: Artificial sequence
<220> FEATURE:
<223> OTHER INFORMATION: FnbA.4

<400> SEQUENCE: 5

Gly Leu Gly Thr Glu Asn Gly His Gly Asn Tyr Gly Val Ile Glu Glu
1               5                   10                  15

Ile Glu Glu Asn Ser His Val Asp Ile Lys
            20                  25

<210> SEQ ID NO 6
<211> LENGTH: 26
<212> TYPE: PRT
<213> ORGANISM: Artificial sequence
<220> FEATURE:
<223> OTHER INFORMATION: FnbA.5

<400> SEQUENCE: 6

Lys Tyr Glu Gln Gly Gly Asn Ile Val Asp Ile Asp Phe Asp Ser Val
1               5                   10                  15

Pro Gln Ile Gln Gly Gln Asn Asn Gly Asn
            20                  25

<210> SEQ ID NO 7
<211> LENGTH: 26
<212> TYPE: PRT
<213> ORGANISM: Artificial sequence
<220> FEATURE:
<223> OTHER INFORMATION: FnbA.6

<400> SEQUENCE: 7

Lys Tyr Glu Gln Gly Gly Asn Ile Ile Asp Ile Asp Phe Asp Ser Val
1               5                   10                  15

Pro Gln Ile His Gly Phe Asn Lys His Thr
            20                  25

<210> SEQ ID NO 8
<211> LENGTH: 26
<212> TYPE: PRT
<213> ORGANISM: Artificial sequence
<220> FEATURE:
<223> OTHER INFORMATION: FnbA.7

<400> SEQUENCE: 8

Gly Gly His Asn Ser Val Asp Phe Glu Glu Asp Thr Leu Pro Lys Val
1               5                   10                  15

Ser Gly Gln Asn Glu Gly Gln Gln Thr Ile

```
            20                  25

<210> SEQ ID NO 9
<211> LENGTH: 206
<212> TYPE: PRT
<213> ORGANISM: Artificial sequence
<220> FEATURE:
<223> OTHER INFORMATION: Synthetic

<400> SEQUENCE: 9

Ser Val Phe Leu Gly Thr Met Ile Val Val Gly Met Gly Gln Glu Lys
 1               5                  10                  15

Glu Ala Ala Ala Ser Glu Gln Asn Asn Thr Ile Lys Pro Gly Asp Tyr
            20                  25                  30

Phe Asp Phe Thr Leu Ser Asn Asn Val Glu Thr His Gly Ile Ser Pro
        35                  40                  45

Leu Arg Ser Glu Pro Ile Glu Leu Asp Ile Lys Ser Glu Pro Pro Val
    50                  55                  60

Glu Lys His Glu Leu Thr Gly Thr Ile Glu Glu Ser Asn Asp Ser Lys
65                  70                  75                  80

Pro Ile Asp Phe Glu Tyr His Thr Ala Val Glu Gly Val Glu Gly His
                85                  90                  95

Ala Glu Gly Leu Gly Thr Glu Asn Gly His Gly Asn Tyr Gly Val Ile
            100                 105                 110

Glu Glu Ile Glu Glu Asn Ser His Val Asp Ile Lys Glu Glu Asp Lys
        115                 120                 125

Pro Lys Tyr Glu Gln Gly Gly Asn Ile Val Asp Ile Asp Phe Asp Ser
    130                 135                 140

Val Pro Gln Ile His Gly Gln Asn Lys Gly Asp Tyr Glu His Gly Gly
145                 150                 155                 160

Asn Ile Ile Asp Ile Asp Phe Asp Ser Val Pro His Ile His Gly Phe
                165                 170                 175

Asn Lys His Thr Gly Gly His Asn Ser Val Asp Phe Glu Glu Asp Thr
            180                 185                 190

Leu Pro Gln Val Ser Gly His Asn Glu Gly Gln Gln Thr Ile
        195                 200                 205

<210> SEQ ID NO 10
<211> LENGTH: 26
<212> TYPE: PRT
<213> ORGANISM: Artificial sequence
<220> FEATURE:
<223> OTHER INFORMATION: FnbB.1

<400> SEQUENCE: 10

Ser Val Phe Leu Gly Thr Met Ile Val Val Gly Met Gly Gln Glu Lys
 1               5                  10                  15

Glu Ala Ala Ala Ser Glu Gln Asn Asn Thr
            20                  25

<210> SEQ ID NO 11
<211> LENGTH: 24
<212> TYPE: PRT
<213> ORGANISM: Artificial sequence
<220> FEATURE:
<223> OTHER INFORMATION: FnbB.2

<400> SEQUENCE: 11

Ile Lys Pro Gly Asp Tyr Phe Asp Phe Thr Leu Ser Asn Asn Val Glu
 1               5                  10                  15
```

```
Thr His Gly Ile Ser Pro Leu Arg
            20

<210> SEQ ID NO 12
<211> LENGTH: 48
<212> TYPE: PRT
<213> ORGANISM: Artificial sequence
<220> FEATURE:
<223> OTHER INFORMATION: FnbB.3 and 4

<400> SEQUENCE: 12

Ser Glu Pro Ile Glu Leu Asp Ile Lys Ser Glu Pro Val Glu Lys
1               5                   10                  15

His Glu Leu Thr Gly Thr Ile Glu Glu Ser Asn Asp Ser Lys Pro Ile
            20                  25                  30

Asp Phe Glu Tyr His Thr Ala Val Glu Gly Val Glu Gly His Ala Glu
        35                  40                  45

<210> SEQ ID NO 13
<211> LENGTH: 26
<212> TYPE: PRT
<213> ORGANISM: Artificial sequence
<220> FEATURE:
<223> OTHER INFORMATION: FnbB.5

<400> SEQUENCE: 13

Gly Leu Gly Thr Glu Asn Gly His Gly Asn Tyr Gly Val Ile Glu Glu
1               5                   10                  15

Ile Glu Glu Asn Ser His Val Asp Ile Lys
            20                  25

<210> SEQ ID NO 14
<211> LENGTH: 31
<212> TYPE: PRT
<213> ORGANISM: Artificial sequence
<220> FEATURE:
<223> OTHER INFORMATION: FnbB.6

<400> SEQUENCE: 14

Glu Glu Asp Lys Pro Lys Tyr Glu Gln Gly Gly Asn Ile Val Asp Ile
1               5                   10                  15

Asp Phe Asp Ser Val Pro Gln Ile His Gly Gln Asn Lys Gly Asp
            20                  25                  30

<210> SEQ ID NO 15
<211> LENGTH: 25
<212> TYPE: PRT
<213> ORGANISM: Artificial sequence
<220> FEATURE:
<223> OTHER INFORMATION: FnbB.7

<400> SEQUENCE: 15

Tyr Glu His Gly Gly Asn Ile Ile Asp Ile Asp Phe Asp Ser Val Pro
1               5                   10                  15

His Ile His Gly Phe Asn Lys His Thr
            20                  25

<210> SEQ ID NO 16
<211> LENGTH: 26
<212> TYPE: PRT
<213> ORGANISM: Artificial sequence
<220> FEATURE:
<223> OTHER INFORMATION: FnbB.8
```

<400> SEQUENCE: 16

Gly Gly His Asn Ser Val Asp Phe Glu Glu Asp Thr Leu Pro Gln Val
1               5                   10                  15

Ser Gly His Asn Glu Gly Gln Gln Thr Ile
            20                  25

<210> SEQ ID NO 17
<211> LENGTH: 182
<212> TYPE: PRT
<213> ORGANISM: Artificial sequence
<220> FEATURE:
<223> OTHER INFORMATION: Synthetic

<400> SEQUENCE: 17

Thr Asn Gln Leu Thr Asn Val Thr Val Gly Ile Asp Ser Gly Asp Thr
1               5                   10                  15

Val Tyr Pro His Gln Ala Gly Tyr Val Lys Gly Val Ile Asp Ser Asp
            20                  25                  30

Gly Asn Val Ile Tyr Thr Phe Thr Asp Tyr Val Asp Thr Lys Glu Asn
        35                  40                  45

Val Thr Ala Asn Ile Thr Met Pro Ala Tyr Ile Asp Pro Glu Asn Val
50                  55                  60

Thr Lys Thr Gly Asn Val Thr Leu Thr Thr Gly Ile Gly Ser Asn Phe
65                  70                  75                  80

Glu Asp Val Thr Asn Ser Val Asn Ile Thr Phe Pro Asn Pro Asn Gln
                85                  90                  95

Tyr Lys Val Glu Phe Asn Thr Pro Thr Leu Asp Leu Pro Gln Ser Ser
            100                 105                 110

Pro Gln Thr Ile Ser Asn Ala Gln Gly Thr Ser Lys Pro Ser Val Arg
        115                 120                 125

Thr Arg Ala Lys Asp Phe Gln Leu Glu Lys Thr Thr Phe Asp Pro Asn
130                 135                 140

Gln Ser Gly Asn Thr Phe Met Ala Ala Asn Phe Thr Phe Ser Leu Pro
145                 150                 155                 160

Leu Phe Thr Asp Arg Ala Lys Ala Pro Lys Ser Gly Thr Tyr Asp Ala
                165                 170                 175

Asn Ile Asn Ile Ala Asp
            180

<210> SEQ ID NO 18
<211> LENGTH: 26
<212> TYPE: PRT
<213> ORGANISM: Artificial sequence
<220> FEATURE:
<223> OTHER INFORMATION: ClfA.1

<400> SEQUENCE: 18

Thr Asn Gln Leu Thr Asn Val Thr Val Gly Ile Asp Ser Gly Asp Thr
1               5                   10                  15

Val Tyr Pro His Gln Ala Gly Tyr Val Lys
            20                  25

<210> SEQ ID NO 19
<211> LENGTH: 26
<212> TYPE: PRT
<213> ORGANISM: Artificial sequence
<220> FEATURE:
<223> OTHER INFORMATION: ClfA.2

<400> SEQUENCE: 19

Gly Val Ile Asp Ser Asp Gly Asn Val Ile Tyr Thr Phe Thr Asp Tyr
1               5                   10                  15

Val Asp Thr Lys Glu Asn Val Thr Ala Asn
            20                  25

<210> SEQ ID NO 20
<211> LENGTH: 26
<212> TYPE: PRT
<213> ORGANISM: Artificial sequence
<220> FEATURE:
<223> OTHER INFORMATION: ClfA.3

<400> SEQUENCE: 20

Ile Thr Met Pro Ala Tyr Ile Asp Pro Glu Asn Val Thr Lys Thr Gly
1               5                   10                  15

Asn Val Thr Leu Thr Thr Gly Ile Gly Ser
            20                  25

<210> SEQ ID NO 21
<211> LENGTH: 26
<212> TYPE: PRT
<213> ORGANISM: Artificial sequence
<220> FEATURE:
<223> OTHER INFORMATION: ClfA.4

<400> SEQUENCE: 21

Asn Phe Glu Asp Val Thr Asn Ser Val Asn Ile Thr Phe Pro Asn Pro
1               5                   10                  15

Asn Gln Tyr Lys Val Glu Phe Asn Thr Pro
            20                  25

<210> SEQ ID NO 22
<211> LENGTH: 26
<212> TYPE: PRT
<213> ORGANISM: Artificial sequence
<220> FEATURE:
<223> OTHER INFORMATION: ClfB.1

<400> SEQUENCE: 22

Thr Leu Asp Leu Pro Gln Ser Ser Pro Gln Thr Ile Ser Asn Ala Gln
1               5                   10                  15

Gly Thr Ser Lys Pro Ser Val Arg Thr Arg
            20                  25

<210> SEQ ID NO 23
<211> LENGTH: 26
<212> TYPE: PRT
<213> ORGANISM: Artificial sequence
<220> FEATURE:
<223> OTHER INFORMATION: ClfB.2

<400> SEQUENCE: 23

Ala Lys Asp Phe Gln Leu Glu Lys Thr Thr Phe Asp Pro Asn Gln Ser
1               5                   10                  15

Gly Asn Thr Phe Met Ala Ala Asn Phe Thr
            20                  25

<210> SEQ ID NO 24
<211> LENGTH: 26
<212> TYPE: PRT
<213> ORGANISM: Artificial sequence
<220> FEATURE:
<223> OTHER INFORMATION: ClfB.3

```
<400> SEQUENCE: 24

Phe Ser Leu Pro Leu Phe Thr Asp Arg Ala Lys Ala Pro Lys Ser Gly
1               5                   10                  15

Thr Tyr Asp Ala Asn Ile Asn Ile Ala Asp
            20                  25

<210> SEQ ID NO 25
<211> LENGTH: 225
<212> TYPE: PRT
<213> ORGANISM: Artificial sequence
<220> FEATURE:
<223> OTHER INFORMATION: Synthetic

<400> SEQUENCE: 25

Leu Thr Ser Glu Leu Asn Thr Gln Ser Glu Thr Val Gly Asn Gln Asn
1               5                   10                  15

Ser Thr Thr Ile Glu Ala Ser Thr Ser Thr Trp Ile Ala Lys Ser Gly
            20                  25                  30

Thr Thr Asn Phe Ser Leu Ser Met Thr Ala Ser Thr Gly Gly Ala Thr
        35                  40                  45

Asn Leu Gln Gln Val Thr Gly Leu Pro Ser Gly Leu Thr Phe Asp Ser
    50                  55                  60

Thr Asn Asn Thr Ile Ser Gly Thr Pro Thr Asn Ile Gly Thr Val Ser
65                  70                  75                  80

Leu Ser Asp Ser Val Ser Ala Ser Lys Ser Leu Ser Thr Ser Glu Ser
                85                  90                  95

Asn Ser Val Ser Ser Ser Thr Ser Thr Ser Leu Val Asn Ser Gln Ser
            100                 105                 110

Val Ser Ser Ser Met Ser Asp Ser Gly Ser Gln Ser Met Ser Asp Ser
        115                 120                 125

Val Ser Thr Ser Asp Ser Ser Ser Leu Ser Val Ser Thr Ser Leu Arg
    130                 135                 140

Ser Ser Ala Ser Glu Ser Asp Ser Met Ser Thr Ser Asp Ser Ser Ser
145                 150                 155                 160

Ile Ser Gly Ser Asn Ser Thr Ser Thr Ser Leu Ser Thr Ile Ser Ile
                165                 170                 175

Ser Gly Ser Gln Ser Thr Val Glu Ser Glu Ser Thr Ser Asp Ser Thr
            180                 185                 190

Ser Ile Ser Asp Ser Glu Ser Glu Ser Val Ser Thr Ser Thr Ser
        195                 200                 205

Thr Ser Leu Ser Thr Ser Asp Ser Thr Ser Thr Ser Glu Ser Leu Ser
    210                 215                 220

Thr
225

<210> SEQ ID NO 26
<211> LENGTH: 26
<212> TYPE: PRT
<213> ORGANISM: Artificial sequence
<220> FEATURE:
<223> OTHER INFORMATION: SraP.1

<400> SEQUENCE: 26

Leu Thr Ser Glu Leu Asn Thr Gln Ser Glu Thr Val Gly Asn Gln Asn
1               5                   10                  15

Ser Thr Thr Ile Glu Ala Ser Thr Ser Thr
            20                  25
```

```
<210> SEQ ID NO 27
<211> LENGTH: 26
<212> TYPE: PRT
<213> ORGANISM: Artificial sequence
<220> FEATURE:
<223> OTHER INFORMATION: SraP.2

<400> SEQUENCE: 27

Trp Ile Ala Lys Ser Gly Thr Thr Asn Phe Ser Leu Ser Met Thr Ala
1               5                   10                  15

Ser Thr Gly Gly Ala Thr Asn Leu Gln Gln
            20                  25

<210> SEQ ID NO 28
<211> LENGTH: 26
<212> TYPE: PRT
<213> ORGANISM: Artificial sequence
<220> FEATURE:
<223> OTHER INFORMATION: SraP.3

<400> SEQUENCE: 28

Val Thr Gly Leu Pro Ser Gly Leu Thr Phe Asp Ser Thr Asn Asn Thr
1               5                   10                  15

Ile Ser Gly Thr Pro Thr Asn Ile Gly Thr
            20                  25

<210> SEQ ID NO 29
<211> LENGTH: 41
<212> TYPE: PRT
<213> ORGANISM: Artificial sequence
<220> FEATURE:
<223> OTHER INFORMATION: SraP.4

<400> SEQUENCE: 29

Val Ser Leu Ser Asp Ser Val Ser Ala Ser Lys Ser Leu Ser Thr Ser
1               5                   10                  15

Glu Ser Asn Ser Val Ser Ser Thr Ser Thr Ser Leu Val Asn Ser
            20                  25                  30

Gln Ser Val Ser Ser Ser Met Ser Asp
        35                  40

<210> SEQ ID NO 30
<211> LENGTH: 26
<212> TYPE: PRT
<213> ORGANISM: Artificial sequence
<220> FEATURE:
<223> OTHER INFORMATION: SraP.5

<400> SEQUENCE: 30

Ser Gly Ser Gln Ser Met Ser Asp Ser Val Thr Ser Asp Ser Ser
1               5                   10                  15

Ser Leu Ser Val Ser Thr Ser Leu Arg Ser
            20                  25

<210> SEQ ID NO 31
<211> LENGTH: 28
<212> TYPE: PRT
<213> ORGANISM: Artificial sequence
<220> FEATURE:
<223> OTHER INFORMATION: SraP.6

<400> SEQUENCE: 31

Ser Ala Ser Glu Ser Asp Ser Met Ser Thr Ser Asp Ser Ser Ser Ile
1               5                   10                  15
```

Ser Gly Ser Asn Ser Thr Ser Thr Ser Leu Ser Thr
            20                  25

<210> SEQ ID NO 32
<211> LENGTH: 26
<212> TYPE: PRT
<213> ORGANISM: Artificial sequence
<220> FEATURE:
<223> OTHER INFORMATION: SraP.7

<400> SEQUENCE: 32

Ile Ser Ile Ser Gly Ser Gln Ser Thr Val Glu Ser Glu Ser Thr Ser
1               5                   10                  15

Asp Ser Thr Ser Ile Ser Asp Ser Glu Ser
            20                  25

<210> SEQ ID NO 33
<211> LENGTH: 26
<212> TYPE: PRT
<213> ORGANISM: Artificial sequence
<220> FEATURE:
<223> OTHER INFORMATION: SraP.8

<400> SEQUENCE: 33

Ser Glu Ser Val Ser Thr Ser Thr Ser Thr Ser Leu Ser Thr Ser Asp
1               5                   10                  15

Ser Thr Ser Thr Ser Glu Ser Leu Ser Thr
            20                  25

<210> SEQ ID NO 34
<211> LENGTH: 193
<212> TYPE: PRT
<213> ORGANISM: Artificial sequence
<220> FEATURE:
<223> OTHER INFORMATION: Synthetic

<400> SEQUENCE: 34

Pro Gln Gly Tyr Gly Ser Tyr Asn Ser Phe Ser Ile Asn Tyr Lys Thr
1               5                   10                  15

Lys Ile Thr Asn Glu Gln Gln Lys Glu Phe Asn Lys Asn Ala Phe Ala
            20                  25                  30

Met Asp Lys Ser His Pro Glu Pro Ile Glu Asp Asn Asp Lys His Glu
        35                  40                  45

Thr Ile Lys Glu Leu Thr Ile Ala Ala Ile Gly Ile Thr Thr Thr Thr
    50                  55                  60

Ile Ala Ser Thr Ala Asp Ala Ser Glu Gly Tyr Gly Pro Arg Glu Lys
65                  70                  75                  80

Lys Pro Val Ser Ile Asn His Asn Ile Asp Tyr Asn Ile Leu Glu Phe
                85                  90                  95

Asn Asp Gly Thr Phe Glu Tyr Gly Ala Arg Pro Gln Phe Asn Lys Pro
            100                 105                 110

Ala Ala Lys Val Pro Ser Gly Ala Ser Thr Gly Glu His Glu Ala Val
        115                 120                 125

Glu Leu Arg Asp Gly Asp Lys Ser Arg Tyr Leu Gly Lys Lys Arg Gly
    130                 135                 140

Leu Glu Thr Ala Val Gly Asp Glu Gly Phe Ala Pro Lys Phe Glu
145                 150                 155                 160

Gly Thr Glu Asp Ala Val Glu Glu Phe Tyr Glu Asn Gly Val Tyr Asp
                165                 170                 175

Tyr Ser Lys Phe Glu Gly Glu His Gly Ala Lys Arg Thr Ala Ala Glu
            180                 185                 190

Gln

<210> SEQ ID NO 35
<211> LENGTH: 26
<212> TYPE: PRT
<213> ORGANISM: Artificial sequence
<220> FEATURE:
<223> OTHER INFORMATION: Cna.1

<400> SEQUENCE: 35

Pro Gln Gly Tyr Gly Ser Tyr Asn Ser Phe Ser Ile Asn Tyr Lys Thr
1               5                   10                  15

Lys Ile Thr Asn Glu Gln Gln Lys Glu Phe
            20                  25

<210> SEQ ID NO 36
<211> LENGTH: 26
<212> TYPE: PRT
<213> ORGANISM: Artificial sequence
<220> FEATURE:
<223> OTHER INFORMATION: EbpS.1

<400> SEQUENCE: 36

Asn Lys Asn Ala Phe Ala Met Asp Lys Ser His Pro Glu Pro Ile Glu
1               5                   10                  15

Asp Asn Asp Lys His Glu Thr Ile Lys Glu
            20                  25

<210> SEQ ID NO 37
<211> LENGTH: 37
<212> TYPE: PRT
<213> ORGANISM: Artificial sequence
<220> FEATURE:
<223> OTHER INFORMATION: Efb.1

<400> SEQUENCE: 37

Leu Thr Ile Ala Ala Ile Gly Ile Thr Thr Thr Thr Ile Ala Ser Thr
1               5                   10                  15

Ala Asp Ala Ser Glu Gly Tyr Gly Pro Arg Glu Lys Lys Pro Val Ser
            20                  25                  30

Ile Asn His Asn Ile
        35

<210> SEQ ID NO 38
<211> LENGTH: 26
<212> TYPE: PRT
<213> ORGANISM: Artificial sequence
<220> FEATURE:
<223> OTHER INFORMATION: Efb.2

<400> SEQUENCE: 38

Asp Tyr Asn Ile Leu Glu Phe Asn Asp Gly Thr Phe Glu Tyr Gly Ala
1               5                   10                  15

Arg Pro Gln Phe Asn Lys Pro Ala Ala Lys
            20                  25

<210> SEQ ID NO 39
<211> LENGTH: 26
<212> TYPE: PRT
<213> ORGANISM: Artificial sequence
<220> FEATURE:
<223> OTHER INFORMATION: Eno.1

```
<400> SEQUENCE: 39

Val Pro Ser Gly Ala Ser Thr Gly Glu His Glu Ala Val Glu Leu Arg
1               5                   10                  15

Asp Gly Asp Lys Ser Arg Tyr Leu Gly Lys
            20                  25

<210> SEQ ID NO 40
<211> LENGTH: 26
<212> TYPE: PRT
<213> ORGANISM: Artificial sequence
<220> FEATURE:
<223> OTHER INFORMATION: Eno.2

<400> SEQUENCE: 40

Lys Arg Gly Leu Glu Thr Ala Val Gly Asp Glu Gly Gly Phe Ala Pro
1               5                   10                  15

Lys Phe Glu Gly Thr Glu Asp Ala Val Glu
            20                  25

<210> SEQ ID NO 41
<211> LENGTH: 26
<212> TYPE: PRT
<213> ORGANISM: Artificial sequence
<220> FEATURE:
<223> OTHER INFORMATION: Eno.3

<400> SEQUENCE: 41

Glu Phe Tyr Glu Asn Gly Val Tyr Asp Tyr Ser Lys Phe Glu Gly Glu
1               5                   10                  15

His Gly Ala Lys Arg Thr Ala Ala Glu Gln
            20                  25
```